United States Patent
DeLuca et al.

(10) Patent No.: US 8,729,054 B2
(45) Date of Patent: *May 20, 2014

(54) 3-DESOXY-2-METHYLENE-VITAMIN D ANALOGS AND THEIR USES

(71) Applicant: Wisconsin Alumni Research Foundation, Madison, WI (US)

(72) Inventors: Hector F. DeLuca, Deerfield, WI (US); Lori A. Plum, Arena, WI (US); Rafal R. Sicinski, Warsaw (PL); Izabela Sibilska, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/633,975

(22) Filed: Oct. 3, 2012

(65) Prior Publication Data

US 2013/0102567 A1 Apr. 25, 2013

Related U.S. Application Data

(60) Provisional application No. 61/550,127, filed on Oct. 21, 2011.

(51) Int. Cl.
*A61K 31/593* (2006.01)
*C07C 401/00* (2006.01)

(52) U.S. Cl.
USPC .......................................... 514/167; 552/653

(58) Field of Classification Search
USPC .......................................... 514/167; 552/653
See application file for complete search history.

(56) References Cited

U.S. PATENT DOCUMENTS

| | | | |
|---|---|---|---|
| 4,666,634 A | 5/1987 | Miyamoto et al. |
| 5,086,191 A | 2/1992 | DeLuca et al. |
| 5,843,928 A | 12/1998 | DeLuca et al. |
| 5,936,133 A | 8/1999 | DeLuca et al. |
| 5,945,410 A | 8/1999 | DeLuca et al. |
| 6,382,071 B1 | 5/2002 | Bertani |

OTHER PUBLICATIONS

Osterm et al., "24- and 26-homo-1,25-dihyroxyvitamin D3: Preferential Activity in Inducing Differentiation of Human Leukemia Cells HL-60 in vitro", Proc. Natl. Acad. Sci. USA, 1987, 84: 2610-2614.
Perlman et al., "1alpha,25-dihyroxyvitamin D3, A Novel Vitamin D-related Compound with Potential Therapeutic Activity", Tetrahedron Letters, 1990, 31: 1823-1824.
Okano et al., "Regulatory Activites of 2beta-(3-Hydroxypropoxy)-1alpha,25-Dihydroxyvitamin D3, A Novel Synthetic Vitamin D3 Derivative, on Calcium Metabolism", Biochem. Biophys. Res. Commun., 1989, 163(3): 1444-1449.

(Continued)

*Primary Examiner* — Sabiha N Qazi
(74) *Attorney, Agent, or Firm* — Andrus Intellectual Property Law, LLP

(57) ABSTRACT

This invention discloses 3-desoxy-2-methylene-vitamin D analogs, and specifically (20S)-3-desoxy-1α,25-dihydroxy-2-methylene-vitamin $D_3$ and (20R)-3-desoxy-1α,25-dihydroxy-2-methylene-vitamin $D_3$ as well as pharmaceutical uses therefor. These compounds exhibit relatively high binding activity and pronounced activity in arresting the proliferation of undifferentiated cells and inducing their differentiation to monocytes thus evidencing use as anti-cancer agents especially for the treatment or prevention of osteosarcoma, leukemia, colon cancer, breast cancer, skin cancer or prostate cancer. These compounds also exhibit relatively high calcemic activity evidencing use in the treatment of bone diseases.

57 Claims, 10 Drawing Sheets

(56) References Cited

OTHER PUBLICATIONS

Miyamoto et al., "Synthetic Studies of Vitamin D Analogs. XIV. Synthesis and Calcium Regulating Activity of Vitamin D3 Analogs Bearing a Hydroxyalkoxy Group at the 2beta-Position", Chem. Pharm. Bull., 1993, 41(6): 1111-1113.
Nishii et al., "The Development of Vitamin D3 Analogs for the Treatment of Osteoporosis", Osteoporosis International, 1993, 1: 190-193.
Inhoffen et al., "Studies in the Vitamin D Series,XXI: Hydrine Compounds from Bitamin D3", Chemische Berichte, 1957, 90: 664-673.
Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.
Sicinski et al., "New Highly Calcemic 1alpha,25-dihydroxy-19-Norvitamin D3 Compounds with Modified Side Chain: 26,27-dihomo- and 26,27-dimethylene Analogs in 20S-Series", Steroids, 2002, 67: 247-256.
Grzywacz et al., "2-Methylene Analogs of 1alpha-hydroxy-19-norvitamin D3; Synthesis, Biological Activities of Docking to the Ligand Binding Domain of the Rat Vitamin D Receptor", J. Steroid Biochem, 2004, 89-90: 13-17.
Windaus et al., "The Constitution of Vitamin D2: Part II", Annalen der Chemie, 1936, 524: 295-299.
Perlman et al., "Novel Synthesis of 19-Nor-Vitamin D Compounds", Tetrahedron Letters, 1991, 32: 7663-7666.
Posner et al., "Stereocontrolled Total Synthesis of Calcitrol Derivatives: 1,25-Dihydroxy-2-(4'-hydroxybutyl)vitamin D3 Analogs of an Osteoporosis Drug", Journal of Organic Chemistry, 1994, 59: 7855-7861.
Posner et al., "2-Fluoroalkyl A-Ring Analogs of 1,25-Dihyroxyvitamin D3. Stereocontrolled Total Synthesis via Intramolecular and Intermolecular Diels-Alder Cycloadditions. Preliminary Biological Testing", Journal of Organic Chemistry, 1995, 60: 4617-4626.
Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.
Collins et al., "Normal Functional Characteristics of Cultured Human Promyelocytioc Leukemia Cells (HL-60) After Induction of Differentiation by Dimethylsulfoxide", The Journal of Experimental Medicine, 1979, 149: 969-974.
Arbour et al., "A Highly Sensitive Method for Large-Scale Measurements of 1,25-Dihydroxyvitamin D", Analytical Biochemistry, 1998, 255: 148-154.
Barrack et al., "Potential Inhibitors of Vitamin D Metabolism: An Oxa Analogue of Vitamin D", Journal of Organic Chemistry, 1988, 53: 1790-1796.
Choudhry et al., "Synthesis of a Biologically Active Vitamin-D2 Metabolite", Journal of Organic Chemistry, 1993, 58:1496-1500.
Hayashi, et al., "Direct Proline-Catalyzed Asymmetric Alpha-Arninoxylation of Aldehydes and Ketones", Journal of Organic Chemistry, 2004, 69: 15966-5973.
Mascarenas et al., "Palladium-Catalysed Coupling of Vinyl Triflates with Enynes and its Application to the Synthesis of 1Alpha,25-Dihydroxyvitamin D3", Tetrahedron, 1991, 47(20:21): 3485-3498.
Reetz, "Alpha-Methylation of Ketones via Manganese-Enolates: Absence of Undesired Polyalkylation", Tetrahedron Letters, 1993, 34(46): 7395-7398.
Sanches-Abella et al., "Synthesis and Biological Activity of Previtamin D3 Analogues with A-ring Modifications", Bioorganic & Medicinal Chemistry, 2008, 16: 10244-10250.

3-DESOXY-2-METHYLENE-VITAMIN D ANALOGS AND THEIR USES

BACKGROUND OF THE INVENTION

This invention relates to vitamin D compounds, and more particularly to 3-Desoxy-2-Methylene-Vitamin D analogs and their pharmaceutical uses, and especially (20S)-3-desoxy-1α,25-dihydroxy-2-methylene-vitamin $D_3$, its biological activities, and its pharmaceutical uses as well as (20R)-3-desoxy-1α,25-dihydroxy-2-methylene-vitamin $D_3$, its biological activities, and its pharmaceutical uses. This latter compound can also be named simply as 3-desoxy-1α,25-dihydroxy-2-methylene-vitamin $D_3$ since the 20-methyl substituent is in its natural or "R" orientation.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of some 19-nor-analogs (e.g., 1α,25-dihydroxy-19-nor-vitamin $D_3$) revealed a selective activity profile with high potency in inducing cellular differentiation, and reduced calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at both carbon 1 (C-1) and carbon 3 (C-3), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

Analogs of the natural hormone 1α,25-dihydroxyvitamin $D_3$ characterized by the transposition of the A-ring exocyclic methylene group from carbon 10 (C-10) to carbon 2 (C-2) (e.g., 1α,25-dihydroxy-2-methylene-19-nor-vitamin D analogs) have been synthesized and tested [see Sicinski et al., J. Med. Chem., 41, 4662 (1998); Sicinski et al., Steroids 67, 247 (2002); and, DeLuca et al., U.S. Pat. Nos. 5,843,928; 5,936,133 and 6,382,071)]. Molecular mechanics studies performed on these analogs predict that a change of A-ring conformation may cause flattening of the cyclohexanediol ring. Molecular mechanics calculations and NMR studies also predict that the A-ring conformational equilibrium would be ca. 6:4 in favor of the conformer having an equatorial 1α-OH. It was further predicted that introduction of the 2-methylene group into 19-nor-vitamin D carbon skeleton would change the character of its 1α- and 3β-A-ring hydroxyls. They would both be in allylic positions similar to the 1α-hydroxyl group in the molecule of the natural hormone [i.e., 1α,25-(OH)$_2$D$_3$]. It was found that 1α,25-dihydroxy-2-methylene-19-nor-vitamin D analogs are characterized by significant biological potency. In addition, the biological potency of such analogs may be enhanced dramatically where "unnatural" (20S)-configuration is present.

SUMMARY OF THE INVENTION

The present invention is aimed at vitamin D compounds characterized by not only having the A-ring exocyclic methylene group at carbon 10 (C-10), but also by the presence of an additional exomethylene substituent at carbon 2 (C-2) (i.e., 2-methylene-vitamin D analogs). These analogs also lack a 3β-OH group, but are characterized by the presence of a 1α-OH group, that is important for biological activity. Accordingly, the present invention is directed toward 3-desoxy-2-methylene-vitamin D analogs, and their pharmaceutical uses, and more specifically toward (20S)-3-desoxy-1α,25-dihydroxy-2-methylene-vitamin $D_3$, its biological activity, and various pharmaceutical uses for this compound as well as (20R)-3-desoxy-1α,25-dihydroxy-2-methylene-vitamin $D_3$, its biological activity, and various pharmaceutical uses for this compound.

Structurally these 3-desoxy-2-methylene-vitamin D analogs are characterized by the general formula I shown below:

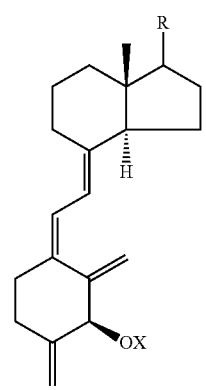

I where X is selected from the group consisting of hydrogen and a hydroxy-protecting group, and where the group R represents any of the typical side chains known for vitamin D type compounds. Thus, R may be hydrogen, an alkyl, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^S$ and a radical of the structure:

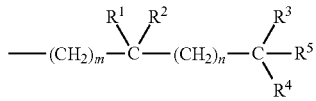

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

Specific important examples of side chains are the structures represented by formulas (a), (b), (c), (d) and (e) below with natural 20R-configuration, i.e., the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

Additional important examples of side chains are the structures represented by formulas (a), (b), (c), (d) and (e) below having the 20-epi or (20S)-configuration, i.e., the side chain as it occurs in (20S)-25-hydroxyvitamin D$_3$ (a); (20S)-vitamin D$_3$ (b); (20S)-25-hydroxyvitamin D$_2$ (c); (20S)-vitamin D$_2$ (d); and the C-24 epimer of (20S)-25-hydroxyvitamin D$_2$ (e).

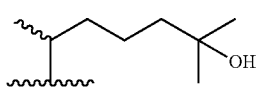

(a)

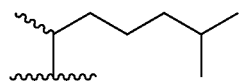

(b)

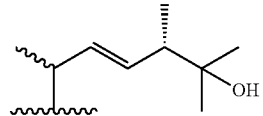

(c)

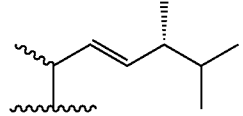

(d)

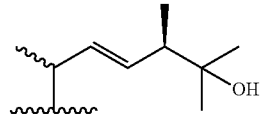

(e)

The wavy line to the carbon 20 indicates that carbon 20 may have either the R or S configuration.

The preferred analogs are (20S)-3-desoxy-1α,25-dihydroxy-2-methylene-vitamin D$_3$ (referred to herein as "3D-QMS") which has the following formula Ia:

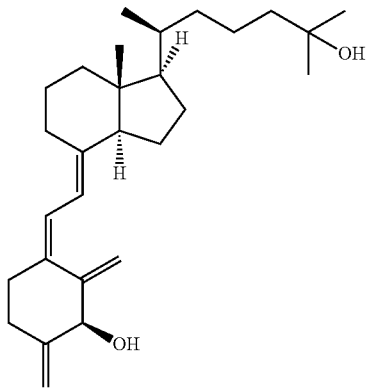

Ia and (20R)-3-desoxy-1α,25-dihydroxy-2-methylene-vitamin D$_3$ (referred to herein as "3D-QM") which has the following formula Ib:

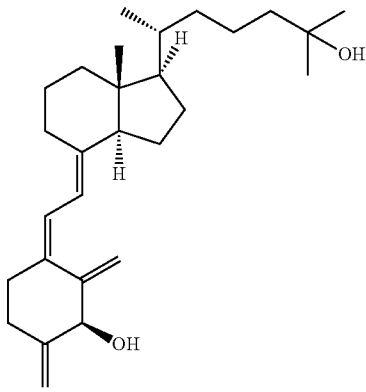

Ib

The above compounds of formula I, especially formula Ia and Ib, exhibit a desired, and highly advantageous, pattern of biological activity. These compounds are characterized by relatively high binding to vitamin D receptors, i.e. they bind with about the same affinity as 1α,25-dihydroxyvitamin $D_3$, and in bone cells their in vitro transcription activity is also substantially the same as 1α,25-dihydroxyvitamin $D_3$ in causing 24-hydroxylase gene transactivation. They are either about the same or more potent causing differentiation of HL-60 cells into monocytes than 1,25$(OH)_2D_3$. They also exhibit either about the same or slightly more activity in their ability to mobilize calcium from bone, and similar or slightly more activity in their ability to promote intestinal calcium transport, as compared to 1α,25-dihydroxyvitamin $D_3$.

The above compounds I, and particularly Ia and Ib, have relatively high binding affinity, are characterized by relatively high cell differentiation activity, and relatively high bone calcium mobilization activity and intestinal calcium transport activity. Thus, these compounds have potential as anti-cancer agents and provide therapeutic agents for the prevention or treatment of osteosarcoma, leukemia, colon cancer, breast cancer, skin cancer and prostate cancer. Because of their selective activity in the bone and relatively high potency on cellular differentiation, 3D-QMS and 3D-QM might also be useful in treatment of bone diseases, such as senile osteoporosis, postmenopausal osteoporosis, steroid-induced osteoporosis, low bone turnover osteoporosis, osteomalacia, and renal osteodystrophy.

One or more of the compounds may be present in a composition to treat or prevent the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually, or parenterally in dosages of from about 0.01 μg/day to about 1000 m/day, preferably from about 0.1 μg/day to about 500 μg/day.

BRIEF DESCRIPTION OF THE DRAWINGS

FIG. 1 is a graph illustrating the relative activity of 3D-QMS and 1,25$(OH)_2D_3$ to compete for binding with [$^3$H]-1,25-$(OH)_2D_3$ to the full-length recombinant rat vitamin D receptor;

FIG. 2 is a graph illustrating the percent HL-60 cell differentiation as a function of the concentration of 3D-QMS and 1,25$(OH)_2D_3$;

FIG. 3 is a graph illustrating the in vitro transcription activity of 1,25$(OH)_2D_3$ as compared to 3D-QMS;

FIG. 4 is a bar graph illustrating the bone calcium mobilization activity of 1,25$(OH)_2D_3$ as compared to 3D-QMS; and FIG. 5 is a bar graph illustrating the intestinal calcium transport activity of 1,25$(OH)_2D_3$ as compared to 3D-QMS.

FIG. 6 is a graph illustrating the relative activity of 3D-QM and 1,25$(OH)_2D_3$ to compete for binding with [$^3$H]-1,25-$(OH)_2D_3$ to the full-length recombinant rat vitamin D receptor;

FIG. 7 is a graph illustrating the percent HL-60 cell differentiation as a function of the concentration of 3D-QM and 1,25$(OH)_2D_3$;

FIG. 8 is a graph illustrating the in vitro transcription activity of 1,25$(OH)_2D_3$ as compared to 3D-QM;

FIG. 9 is a bar graph illustrating the bone calcium mobilization activity of 1,25$(OH)_2D_3$ as compared to 3D-QM; and FIG. 10 is a bar graph illustrating the intestinal calcium transport activity of 1,25$(OH)_2D_3$ as compared to 3D-QM.

DETAILED DESCRIPTION OF THE INVENTION

Figure 1:
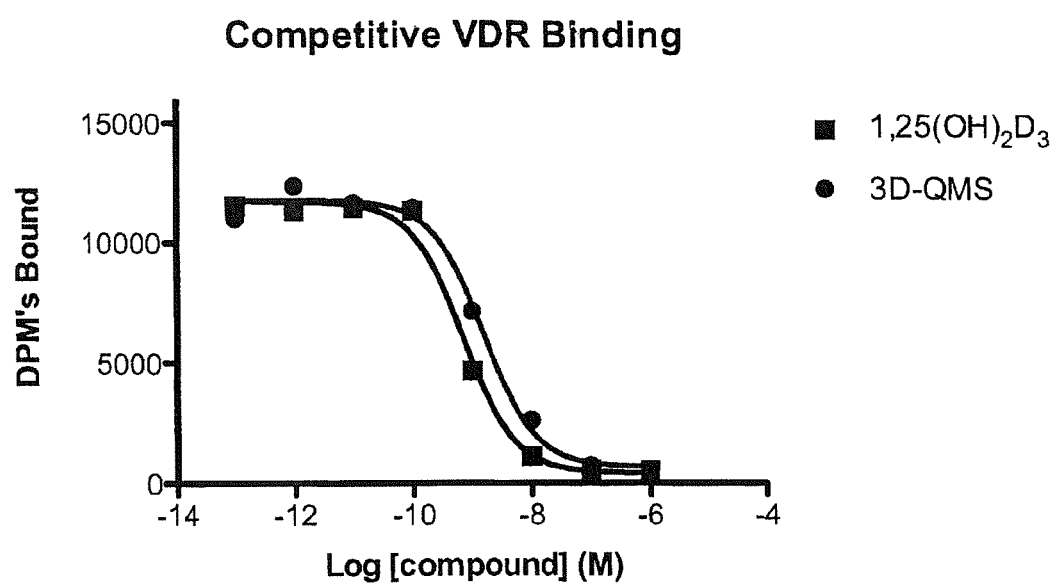
FIGS. 1-5 illustrate various biological activities of (20S)-3-desoxy-1α, 25-dihydroxy-2-methylene-vitamin $D_3$, hereinafter referred to as "3D-QMS," as compared to the native hormone 1α,25-dihydroxyvitamin $D_3$, hereinafter "1,25 $(OH)_2D_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO-groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$—where k is an integer.

The preparation of 2-methylene-vitamin D analogs of the basic structure I can be accomplished by a common general method, i.e., a Sonogashira coupling of a bicyclic vinyl compound II with the dienyne III:

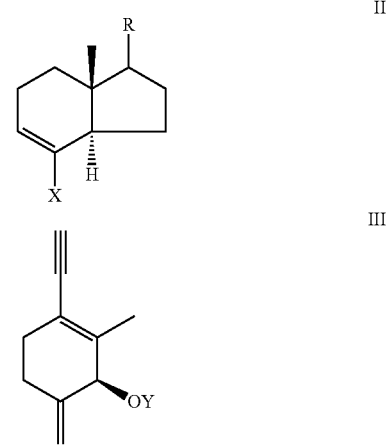

In the structures II and III, group X represents a leaving group selected from halogen (iodine, bromine or chlorine)

and alkyl- or aryl-sulphonyloxy such as mesyloxy, tosyloxy or—most preferably—trifloxy. Groups Y and R represent groups defined above; Y being preferably hydroxy-protecting group, it being also understood that any functionalities in R that might be sensitive, or that interfere with the coupling reaction, be suitable protected as is well-known in the art. The process shown above represents an application of the convergent synthesis concept, which has been applied effectively for the preparation of vitamin D compounds [Mascarenas et al., Tetrahedron 47, 3485 (1991), Barrack et al., J. Org. Chem., 53, 1790 (1988); Sanchez-Abella et al., Bioorg. Med. Chem. 16, 10244 (2008)].

Bicyclic compounds of the general structure II are known, or can be easily prepared by known methods from the corresponding Windaus-Grundmann type ketones. Specific important examples of such known bicyclic ketones are the structures with the side chains (h), (i), (j), (k), (l), (m), and (n) below described above, i.e., 25-hydroxy Grundmann's ketone (h) [Baggiolini et al., J. Org. Chem., 51, 3098 (1986)]; Grundmann's ketone (i) [Inhoffen et al., Chem. Ber., 90, 664 (1957)]; 25-hydroxy Windaus ketone (j) [Baggiolini et al., J. Org. Chem., 51, 3098 (1986)]; Windaus ketone (k) [Windaus et al., Ann., 524, 297 (1936)]; (20S)-25-hydroxy Grundmann's ketone (l) [Sicinski et al., J. Med. Chem., 41, 4662 (1998)]; (20S)-Grundmann's ketone (m) [Grzywacz et al., J. Steroid Biochem. Mol. Biol., 89-90, 13 (2004)]; and (20S)-25-methyl Grundmann's ketone (n) [Grzywacz et al., J. Steroid Biochem. Mol. Biol., 89-90, 13 (2004)]:

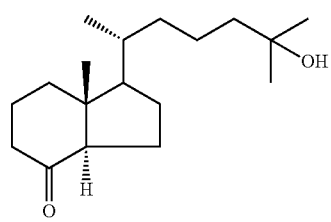

(h)

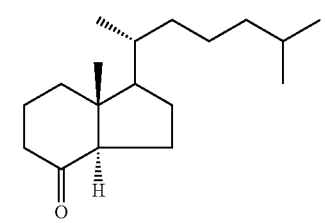

(i)

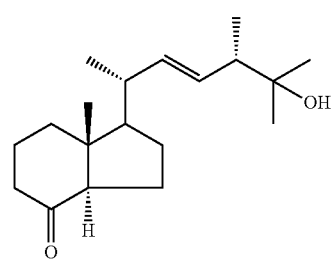

(j)

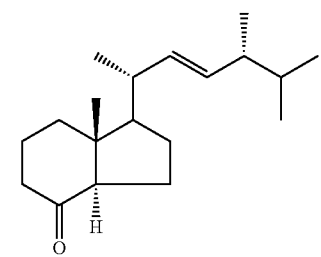

(k)

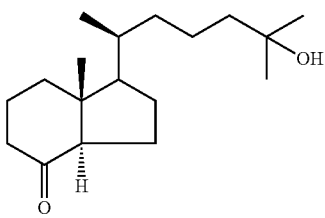

(l)

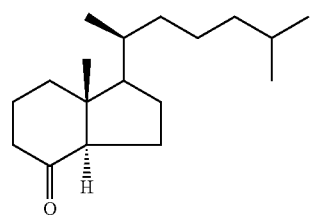

(m)

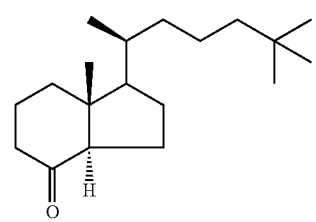

(n)

Regarding the preparation of the dienynes of the structure III, new synthetic route was established. As set forth in SCHEME I, an achiral, commercially available acetal-ketone 1, was α-methylated using the method of Reetz et al. [Tetr. Lett., 34, 7395 (1993)]. Then, the keto group in the formed 2 was reduced and the obtained alcohol 3 (a diastereomeric mixture) was subsequently esterified with pivaloyl chloride. Only the prevailing trans-isomer underwent this reaction and, therefore, the resulted ester 4 was a mixture of (S,S)- and (R,R)-enantiomers. The carbonyl group in 4 was deprotected in the reaction with the Lewis acid (FeCl$_3$) and the formed cyclohexanone 5 was diastereoselectively α-hydroxylated using the method elaborated by Hayashi et al. [J. Org. Chem., 69, 5966 (2004)] and involving the reaction of a ketone with nitrosobenzene in the presence of a catalytic amount of L-proline. Three main products 6a,b,c were isolated in comparable quantities. The introduced secondary hydroxyl in the product 6c was silylated and the protected compound 7 was subjected to the Wittig reaction with an ylide generated from methyltriphenylphosphonium bromide and n-butyllithium. The pivaloyl protecting group in the formed olefin 8 was removed by treatment with DIBALH and the obtained cyclohexanol derivative 9 was oxidized to the ketone 10. Its reaction with lithium acetylide provided tertiary alcohol 11 which was dehydrated with Martin's sulfurane dehydrating reagent. After removal of the TMS group from the ethynyl substituent in the obtained product 12, the desired A-ring fragment 13 was prepared.

SCHEME II shows the subsequent Sonogashira coupling of the obtained A-ring dienyne 13 with an enol triflate 14 [Sanchez-Abella et al., Bioorg. Med. Chem. 16, 10244 (2008)], representing C,D-fragment derived from the protected 25-hydroxy Grundmann's ketone. The reaction should be preferentially carried out in the presence of bis(triphenylphosphine)palladium (II) acetate-copper (I) iodide catalyst and diethylamine. The coupling resulted in formation of the trienyne 15 which was further hydrogenated in the presence of Lindlar catalyst and quinoline. The expected product of such catalytic hydrogenation, previtamin D compound 16, was then subjected to the thermal reaction in hexane. The protected vitamin D compound 17 was isolated by HPLC, and after hydroxyls deprotection with tetrabutylammonium fluoride provided the desired 3-desoxy-1α, 25-dihydroxy-2-methylene-vitamin $D_3$ (18). This synthetic path is described in EXAMPLE I herein.

SCHEME III shows a preparation of the enol triflate 20, representing a C,D-fragment, from the protected (20S)-25-hydroxy Grundmann's ketone 19 [Sicinski et al., J. Med. Chem., 41, 4662 (1998)]. Treatment of the enol form of 19, generated by addition of the LDA at −78° C., with N-phenyltriflimide afforded 20. The subsequent Sonogashira coupling of the obtained A-ring dienyne 13 with an enol triflate 20 resulted in formation of the trienyne 21 which was further hydrogenated in the presence of Lindlar catalyst and quinoline. The expected product of such catalytic hydrogenation, previtamin D compound 22, was subjected to the thermal reaction in hexane. The obtained protected vitamin D compound 23 after hydroxyls deprotection with tetrabutylammonium fluoride provided the desired (20S)-3-desoxy-1α,25-dihydroxy-2-methylene-vitamin $D_3$ (24). This synthetic path is described in EXAMPLE II herein.

As it is evident from EXAMPLE I and EXAMPLE II, other vitamin D analogs having the different side-chains may be synthesized by the methods set forth herein. This invention is described by the following illustrative examples. In these examples specific products identified by Arabic numerals (e.g., 1, 2, 3, etc) refer to the specific structures so identified in the preceding description and in the SCHEME I, SCHEME II and SCHEME III.

EXAMPLES

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 200, 400 and 500 MHz with a Varian Unity, Bruker DMX-400 and Bruker DMX-500 spectrometers, respectively. $^{13}$C nuclear magnetic resonance (NMR) spectra were recorded in deuteriochloroform at 50, 100 and 125 MHz with a Varian Unity, Bruker DMX-400 and Bruker DMX-500 spectrometers, respectively. Chemical shifts (δ) were reported downfield from internal Me$_4$Si (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

In the description of the proton MMR signals of compounds 6a-6c orientation of the hydroxyl group introduced in the proline-catalyzed process was arbitrarily established as "α"; the same assignment was used for their derivatives 7-13.

Example I

Preparation of
3-desoxy-1α,25-dihydroxy-2-methylene-vitamin $D_3$
(18)

(a) α-Methylation of a ketone 1 (SCHEME I). 7-Methyl-1,4-dioxa-spiro[4.5]decan-8-one (2). A solution of 1,4-cyclohexanedione monoethylene ketal (1, 5.12 g, 32.96 mmol) in dry THF (20 mL) was added to a solution of LiHMDS (1.0 M in THF, 33.0 mL, 33.0 mmol) under argon at −78° C. and the mixture was stirred for 40 min. After warming up to room temperature DMPU (13.3 mL) was added. Stirring was continued for additional 10 min, and the enolate solution was cannulated to the flask containing anhydrous MnBr$_2$ (7.83 g, 36.46 mmol) and the mixture was stirred until clear reddish-brown solution was obtained (approximately 30 min). The methyl iodide (2.5 mL, 40.0 mmol) was then added, and after 4 h the reaction was quenched by the addition of saturated NH$_4$Cl and EDTA. Materials were extracted with diethyl ether, dried over MgSO$_4$, and concentrated. Purification by column chromatography on silica (3→5% ethyl acetate/hexane gradient) gave an oily α-methyl ketone 2 (3.72 g, 67%).

2: $^1$H NMR (200 MHz, CDCl$_3$) δ 1.02 (3H, d, J=6.6 Hz, CH$_3$), 1.72 (1H, br t, J=13.2 Hz), 2.04 (3H, br m), 2.35 (1H, ddd, J=14.4, 4.9, 2.9 Hz), 2.69 (2H, m), 4.02 (4H, m, O—CH$_2$CH$_2$—O); $^{13}$C NMR (50 MHz, CDCl$_3$) δ 14.48, 34.82, 38.17, 41.44, 42.92, 64.78, 64.90, 107.55, 212.08; HRMS (ESI) exact mass calcd for C$_9$H$_{14}$O$_3$Na (M$^+$+Na) 193.0841, measured 193.0836.

(b) Reduction of the ketone 2. Cis- and trans-7-Methyl-1,4-dioxa-spiro[4.5]decan-8-ols (3). To a solution of ketone (2, 2.99 g, 17.57 mmol) in anhydrous MeOH (83 mL) was slowly added NaBH$_4$ (1.039 g, 27.45 mmol) at 0° C. After 10 min cooling bath was removed, and stirring was continued at room temperature for 1 h. Brine was added and mixture was extracted with ethyl acetate, washed with 2N NaOH solution, dried over MgSO$_4$, and concentrated. The resulted crude mixture of the alcohols 3 (2.87 g, 95%; cis:trans isomer ratio of 1:13.3) was sufficiently pure to be used in the second synthetic step. Separation of the isomers could be achieved by column chromatography on silica using hexane/ethyl acetate (9:1) solvent system.

3 (cis-isomer): $^1$H NMR (200 MHz, CDCl$_3$) δ 0.98 (3H, d, J=6.8 Hz, CH$_3$), 1.4-1.95 (7H, br m), 3.77 (1H, dd, J=4.9, 2.4 Hz, 8-H), 3.94 (4H, br m, O—CH$_2$CH$_2$—O); $^{13}$C NMR (50 MHz, CDCl$_3$) δ 17.90, 28.50, 30.72, 34.33, 37.03, 64.32, 69.24, 76.01, 109.23; HRMS (ESI) exact mass calcd for C$_9$H$_{16}$O$_3$Na (M$^+$+Na) 195.0997, measured 195.1002.

3 (trans-isomer): $^1$H NMR (200 MHz, CDCl$_3$) δ 1.01 (3H, d, J=6.4 Hz, CH$_3$), 1.54-1.97 (7H, br m), 3.19 (1H, dt, J=4.6, 9.8 Hz, 8-H), 3.93 (4H, br s, O—CH$_2$CH$_2$—O); $^{13}$C NMR (50 MHz, CDCl$_3$) δ 18.49, 29.86, 32.41, 33.41, 37.42, 41.53, 64.48, 75.40, 108.54; HRMS (ESI) exact mass calcd for C$_9$H$_{16}$O$_3$Na (M$^+$+Na) 195.0997, measured 195.0999.

(c) Protection of hydroxy group in 3. trans-7-Methyl-8-pivaloyloxy-1,4-dioxa-spiro[4.5]decane (4). Pivaloyl chloride (2.06 mL, 16.74 mmol) was slowly added to a solution of isomeric alcohols 3 (2.86 g, 16.65 mmol; cis:trans 1:13.3) in anhydrous pyridine (30 mL), and the mixture was stirred at 60° C. for 3 h. Heating bath was removed and the mixture was allowed to cool to the room temperature. A solution of HCl (5%) was then added, and the mixture was extracted with ethyl acetate, washed with saturated NaHCO$_3$, dried over MgSO$_4$, and concentrated. Column chromatography on silica using hexane/ethyl acetate (97:3) gave the ester 4 (3.95 g, 97%); further elution with hexane/ethyl acetate (8:2) provided the unreacted alcohol 3 (cis-isomer, 128 mg).

4: $^1$H NMR (200 MHz, CDCl$_3$) δ 0.90 (3H, d, J=6.6 Hz, CH$_3$), 1.19 (9H, s, t-Bu), 1.43 (1H, br t, J=12.9 Hz), 1.52-1.98 (6H, br m), 3.94 (4H, br s, O—CH$_2$CH$_2$—O), 4.41 (1H, dt, J=4.9, 10.3 Hz, 8-H); $^{13}$C NMR (50 MHz, CDCl$_3$) Δ 18.29, 27.33, 28.31, 32.91, 34.63, 39.01, 41.41, 64.51, 64.59, 76.53, 108.23, 178.38; HRMS (ESI) exact mass calcd for C$_{14}$H$_{24}$O$_4$Na (M$^+$+Na) 279.1572, measured 279.1564.

(d) Deprotection of a carbonyl group in the ketal 4. trans-3-Methyl-4-pivaloyloxy-cyclohexanone (5). To a solution of acetal 4 (120 mg, 467.8 μmol) in methylene chloride (13.7 mL) was added $FeCl_3 \times 6H_2O$ (653 mg, 2.42 mmol) at room temperature. The resulting yellowish suspension was stirred for 1.5 h and quenched by the addition of water. The aqueous layer was extracted with methylene chloride, the combined organic layers were dried over $MgSO_4$ and concentrated. The residue was applied on a silica Sep-Pak cartridge and eluted with hexane/ethyl acetate (98:2) to give ketone 5 (84 mg, 96%) as a colorless oil.

5: $^1$H NMR (200 MHz, $CDCl_3$) δ 1.0 (3H, d, J=6.34 Hz, $CH_3$), 1.23 (9H, s, t-Bu), 1.85 (1H, br m), 2.1-2.6 (6H, br m), 4.84 (1H, dt, J=3.7, 7.8 Hz, 8-H); $^{13}$C NMR (50 MHz, $CDCl_3$) δ 18.40, 27.30, 28.63, 36.79, 38.12, 39.06, 45.79, 73.82, 178.02, 209.57; HRMS (ESI) exact mass calcd for $C_{12}H_{20}O_3Na$ ($M^+$+Na) 235.1310, measured 235.1313.

(e) α-Hydroxylation of the ketone 5. To a stirred solution of ketone 5 (551 mg, 2.59 mmol) and L-proline (143.6 mg, 1.25 mmol) in chloroform (5 mL) a solution of nitrosobenzene (485 mg, 4.53 mmol) in chloroform (10 mL) was slowly added by a syringe pump at 4° C. over 24 h. Then the mixture was stirred at room temperature for additional 2 h. Reaction was quenched by the addition of brine and it was extracted with ethyl acetate, dried over $MgSO_4$ and concentrated. Column chromatography on silica using hexane/ethyl acetate (9:1) gave isomeric α-hydroxy ketones (in the elution order): 6c, 6b and 6a (34.5:30.1:35.4; 380 mg, 64%). The compounds were approx. 90% pure (as judged by NMR) and they were used for the next synthetic steps without further purification.

(2R,4R,5R)-2-Hydroxy-5-methyl-4-pivaloyloxy-cyclohexanone (6a): $^1$H NMR (400 MHz, $CDCl_3$) δ 0.97 (3H, d, J=7.3 Hz, $CH_3$), 1.25 (9H, s, t-Bu), 1.89 (1H, ddd, J=14.4, 11.8, 2.6 Hz, 3α-H), 2.32 (1H, br d, J=13.7 Hz, one of 6-H), 2.54 (2H, m, 3β- and 5β-H), 2.86 (1H, dd, J=13.7, 6.0 Hz, one of 6-H), 3.53 (1H, br s, OH), 4.41 (1H, dd, J=11.8, 7.3 Hz, 2β-H), 5.00 (1H, br s, 4α-H); $^{13}$C NMR (125 MHz, $CDCl_3$) δ 17.5, 27.15, 34.97, 35.79, 36.36, 41.17, 71.84, 72.56, 177.65, 209.13; HRMS (ESI) exact mass calcd for $C_{12}H_{20}O_4Na$ ($M^+$+Na) 251.1260, measured 251.1264.

(2R,4S,5S)-2-Hydroxy-5-methyl-4-pivaloyloxy-cyclohexanone (6b): $^1$H NMR (400 MHz, $CDCl_3$) δ 1.03 (3H, d, J=6.4 Hz, $CH_3$), 1.28 (9H, s, t-Bu), 1.56 (1H, q, J~12 Hz, 3α-H), 2.07 (1H, br m), 2.23 (1H, br t, J~14 Hz, 6β-H), 2.57 (1H, dd, J=14.2, 4.3 Hz, 6α-H), 2.66 (1H, ddd, J=11.8, 6.9, 4.0 Hz, 3β-H), 3.45 (1H, br s, OH), 4.22 (1H, dd, J=12.7, 6.9 Hz, 2β-H), 4.88 (1H, dt, J~4, 11 Hz, 4β-H); $^{13}$C NMR (125 MHz, $CDCl_3$) δ 18.20, 27.05, 38.37, 38.83, 39.36, 43.18, 72.12, 72.37, 177.78, 208.51; HRMS (ESI) exact mass calcd for $C_{12}H_{20}O_4Na$ ($M^+$+Na) 251.1260, measured 251.1261.

(2R,3R,4S)-2-Hydroxy-3-methyl-4-pivaloyloxy-cyclohexanone (6c): $^1$H NMR (400 MHz, $CDCl_3$) δ 0.85 (3H, d, J=7.2 Hz, $CH_3$), 1.26 (9H, s, t-Bu), 2.09 (2H, m), 2.45 (1H, br dd, J=14.2, 4.6 Hz), 2.62 (1H, br m), 2.75 (1H, m), 3.51 (1H, br s, OH), 4.61 (1H, d, J=6.3 Hz, 2β-H), 5.07 (1H, narr m, 4α-H); $^{13}$C NMR (125 MHz, $CDCl_3$) δ 11.10, 26.41, 27.14, 34.54, 38.96, 42.45, 72.85, 74.30, 177.37, 210.65; HRMS (ESI) exact mass calcd for $C_{12}H_{20}O_4Na$ ($M^+$+Na) 251.1260, measured 251.1263.

(f) Protection of hydroxy group in 6c. (2R,3R,4S)-2-[(tert-Butyldiphenylsilyl)oxy]-3-methyl-4-pivaloyloxy-cyclohexanone (7). t-BDPSCl (113 μL, 489 mmol) was added to a solution of α-hydroxy ketone 6c (75 mg, 329 μmol) and silver nitrate (170 mg, 1 mmol) in anhydrous DMF (1.6 mL) under argon at room temperature; white precipitate formed immediately. Reaction was stirred for 30 h and then it was quenched by the addition of water. The mixture was extracted with hexane, dried over $MgSO_4$, and concentrated. Purification by column chromatography on silica (1%→4% diethyl ether in hexane) gave protected α-hydroxy ketone 7 (112 mg, 73%).

7: $[α]^{20}_D$-118° (c 2.17, $CHCl_3$); $^1$H NMR (500 MHz, $CDCl_3$) δ 1.00 (3H, d, J=6.0 Hz, $CH_3$), 1.03 (9H, s, Si-t-Bu), 1.11 (9H, s, t-Bu), 1.91 (1H, m), 2.03 (1H, m), 2.29 (2H, m), 2.41 (1H, m), 4.51 (1H, d, J=5.0 Hz, 2β-H), 4.97 (1H, narr m, 4α-H), 7.37 (6H, m, Ar—H), 7.66 (4H, m, Ar—H); $^{13}$C NMR (125 MHz, $CDCl_3$) δ 11.94, 19.52, 25.05, 27.02, 35.75, 38.78, 43.97, 73.14, 76.48, 127.56, 127.72, 129.77, 129.87, 133.18, 133.43, 135.74, 135.96, 177.32, 207.85; HRMS (ESI) exact mass calcd for $C_{28}H_{38}O_4SiNa$ ($M^+$+Na) 489.489.2437, measured 489.2439.

(g) Wittig methylenation of the ketone 7. (2R,3R,4S)-2-[(tert-Butyldiphenylsilyl)oxy]-3-methyl-1-methylene-4-pivaloyloxy-cyclohexane (8). To methyltriphenylphosphonium bromide (60 mg, 168 μmol) in anhydrous THF (0.7 mL) at 0° C. was added dropwise n-BuLi (1.6 M in hexanes; 212 μL, 338.6 μmol). After 15 min another portion of phosphonium salt (60 mg, 168 μmol) was added, and the solution was stirred at 0° C. for 10 min, and at room temperature for 20 min. The orange-red mixture was then cooled to −78° C. and siphoned to the precooled (−78° C.) solution of the ketone 7 (79 mg, 169 μmol) in anhydrous THF (250 μL). The reaction mixture was stirred at −78° C. for 3 h and then at room temperature for 1 h. The mixture was poured into brine and extracted with hexane. The organic layer was dried over $MgSO_4$ and evaporated to give an orange oily residue which was applied on a silica Sep-Pak cartridge. Elution with hexane/diethyl ether (98:2) gave pure olefinic compound 8 (62 mg, 79%) as a colorless oil.

8: $[α]^{20}_D$-132° (c 3.13, $CHCl_3$); $^1$H NMR (400 MHz, $CDCl_3$) δ 0.87 (3H, d, J=7.7 Hz, $CH_3$), 1.05 (9H, s, Si-t-Bu), 1.09 (9H, s, t-Bu), 1.48 (1H, m), 1.82 (2H, m), 2.09 (1H, ddd, J=13.3, 9.7, 4.7 Hz, 6β-H), 2.34 (1H, dt, J=13.3, 5.5 Hz, 6α-H), 4.41 (1H, d, J=3.4 Hz, 2β-H), 4.79 and 4.89 (1H and 1H, each s, =$CH_2$), 4.86 (1H, narr m, 4β-H), 7.36 (6H, m, Ar—H), 7.65 (4H, m, Ar—H); $^{13}$C NMR (100 MHz, $CDCl_3$) δ 11.84, 19.55, 27.06, 27.13, 28.59, 29.08, 38.70, 41.89, 74.41, 74.48, 108.79, 127.35, 127.48, 129.48, 129.60, 133.85, 134.14, 135.91, 147.01, 177.56; HRMS (ESI) exact mass calcd for $C_{29}H_{40}O_3SiNa$ ($M^+$+Na) 487.2645, measured 487.2651.

(h) Reduction of the ester 8. (1S,2R,3R)-3-[(tert-Butyldiphenylsilyl)oxy]-2-methyl-4-methylene-cyclohexanol (9). Diisobutylaluminium hydride (1.0 M in toluene; 2.14 mL, 2.14 mmol) was slowly added to a stirred solution of ester 8 (280 mg, 603 μmol) in toluene:methylene chloride (2:1, 16 mL) at −78° C. under argon. Stirring was continued at −78° C. for 1 h and at −40° C. for 30 min. The mixture was quenched by the addition of potassium-sodium tartrate (2N, 4 mL), aqueous HCl (2N, 4 mL) and $H_2O$ (4 mL), and extracted with ethyl acetate. The organic phase was washed with brine, dried over $MgSO_4$ and evaporated. The residue was purified by column chromatography on silica using hexane/ethyl acetate (9:1) gave alcohol 9 (223 mg, 97%).

9: $[α]^{20}_D$-145° (c 3.3, $CHCl_3$); $^1$H NMR (200 MHz, $CDCl_3$) δ 0.89 (3H, d, J=7.0 Hz, $CH_3$), 1.07 (9H, s, Si-t-Bu), 1.44 (2H, m), 1.91 (1H, m), 2.17 (1H, ddd, J=13.2, 6.8, 4.6 Hz, 5β-H), 2.41 (1H, ddd, J=13.2, 8.8, 4.6 Hz, 5α-H), 3.83 (1H, dt, J=3.6, 7.6 Hz, 1α-H), 4.32 (1H, d, J=3.4 Hz, 3β-H), 4.69 (2H, s, =$CH_2$), 7.38 (6H, m, Ar—H), 7.66 (4H, m, Ar—H); $^{13}$C NMR (50 MHz, $CDCl_3$) δ 13.22, 19.74, 27.37, 29.13, 33.49, 45.74, 72.10, 76.19, 109.09, 127.54, 127.64, 129.73, 129.79, 134.06, 134.57, 136.25, 136.30, 148.33;

HRMS (ESI) exact mass calcd for $C_{24}H_{32}O_2SiNa$ (M$^+$+Na) 403.2070, measured 403.2059.

(i) Oxidation of the cyclohexanol 9. (2S,3R)-3-[(tert-Butyldiphenylsilyl)oxy]-2-methyl-4-methylene-cyclohexanone (10). To a stirred solution of alcohol 9 (198 mg, 1.04 mmol) in anhydrous methylene chloride (6 mL) was added Dess-Martin periodinane (265 mg, 625 μmol) at room temperature under argon. Stirring was continued for 1 h and saturated NaHCO$_3$ was slowly added. The mixture was extracted with methylene chloride, dried over MgSO$_4$ and concentrated. The residue was applied on a silica Sep-Pak cartridge and eluted with hexane/diethyl ether (98:2) to afford ketone 10 (195 mg, 95%) as a colorless oil.

10: $[\alpha]^{20}{}_D$-50° (c 3.0, CHCl$_3$); $^1$H NMR (200 MHz, CDCl$_3$) δ 0.94 (3H, d, J=6.8 Hz, CH$_3$), 1.04 (9H, s, Si-t-Bu), 2.25-2.57 (4H, m), 2.83 (1H, m), 4.37 (1H, d, J=3.0 Hz, 3β-H), 4.76 and 4.82 (1H and 1H, each br s, =CH$_2$), 7.36 (6H, m, Ar—H), 7.61 (4H, m, Ar—H); $^{13}$C NMR (50 MHz, CDCl$_3$) δ11.23, 19.51, 27.05, 29.42, 40.64, 52.02, 79.37, 111.34, 127.40, 127.52, 129.71, 129.74, 133.21, 133.53, 136.02, 136.17, 210.74; HRMS (ESI) exact mass calcd for $C_{24}H_{30}O_2SiNa$ (M$^+$+Na) 401.1913, measured 401.1914.

(j) Conversion of the ketone 10 into hydroxyalkyne 11. (1R,2S, 3R)-3-[(tert-Butyldiphenylsilyl)oxy]-2-methyl-4-methylene-1-[(trimethylsilanyl)ethynyl]cyclohexanol (11). A solution of n-BuLi (1.6 M in hexanes, 334.6 μL, 535.3 μmol) was added dropwise to a solution of trimethylsilylacetylene (78 μL, 551 μmol) in anhydrous THF (2 mL) under argon at 0° C. The solution was stirred for 30 min and cooled to -78° C., then precooled (-78° C.) solution of ketone 10 (162 mg, 427.9 μmol) in dry THF (2 mL) was slowly added. After 15 min the mixture was warmed to 0° C., and stirred for additional 30 min. Reaction was quenched by the addition of water, extracted with ether, dried over MgSO$_4$, and concentrated. The resulting product was applied on a silica Sep-Pak cartridge and eluted with hexane/ethyl acetate (98:2) to afford alcohol 11 (203 mg, 99%) as a colorless oil.

11: $[\alpha]^{20}{}_D$-239° (c 1.53, CHCl$_3$); $^1$H NMR (200 MHz, CDCl$_3$) δ 0.09 (9H, s, 3×SiCH$_3$), 1.08 (9H, s, Si-t-Bu), 1.14 (3H, d, J=7.2 Hz, CH$_3$), 1.74 (2H, m), 2.10 (2H, m), 2.61 (1H, m), 3.90 (1H, OH), 4.27 (1H, d, J=2.2 Hz, 3β-H), 4.52 and 4.65 (1H and 1H, each s, =CH$_2$), 7.37 (6H, m, Ar—H), 7.64 (4H, m, Ar—H); $^{13}$C NMR (50 MHz, CDCl$_3$) δ-0.11, 15.02, 19.41, 27.11, 29.85, 36.71, 45.62, 71.12, 80.14, 108.75, 110.41, 127.35, 127.61, 129.76, 129.88, 132.9, 133.11, 136.12, 146.49; HRMS (ESI) exact mass calcd for $C_{29}H_{40}O_2Si_2Na$ (M$^+$+Na) 499.2465, measured 499.2457.

(k) Dehydration of the alcohol 11. (3S)-3-[(tert-Butyldiphenylsilyl)oxy]-2-methyl-4-methylene-1-[(trimethylsilyl)ethynyl]-cyclohexene (12a) and (5R,6R)-5-[(tert-butyldiphenylsilyl)oxy]-6-methyl-4-methylene-1-[(trimethylsilyl)ethynyl]-cyclohexene (12b). To the solution of alcohol 11 (80 mg, 167.8 μmol) in anhydrous carbon tetrachloride (1.8 mL) at room temperature under argon was added solution of [α,α-bis(trifluoromethyl)benzenemethanolato]diphenylsulfur (167 mg, 248 μmol) in anhydrous carbon tetrachloride (3 mL). Reaction was stirred for 6 h and during this time dehydrating reagent was added twice (in ca. 50 mg portions). Water was added, and the mixture was extracted with methylene chloride, dried over Na$_2$SO$_4$ and concentrated. The resulting product was applied on a silica Sep-Pak cartridge and eluted with hexane/diethyl ether (98:2) to afford the oily isomeric dienynes 12a and 12b (62 mg, 81%; 12a:12b isomer ratio of 1:2).

$^1$H NMR (500 MHz, CDCl$_3$, selected signals); 12a: δ 0.18 (1H, s, 3×SiCH$_3$), 1.83 (1H, s, CH$_3$), 4.14 (0.33H, s, 3β-H), 4.35 and 4.65 (0.33H and 0.33H, each s, =CH$_2$); 12b: δ 0.14 (2H, s, 3×SiCH$_3$), 1.05 (2H, d, J=7.0 Hz, CH$_3$), 4.47 (0.67H, d, J=5.0 Hz, 5β-H), 4.92 and 5.23 (0.67H and 0.67H, each s, =CH$_2$), 5.88 (0.67H, t, J=3.5 Hz, 2-H); HRMS (ESI) exact mass calcd for $C_{29}H_{38}OSi_2Na$ (M$^+$+Na) 481.2359, measured 481.2361.

(l) Removal of TMS group from 12. (3S)-3-[(tert-Butyldiphenylsilyl)oxy]-1-ethynyl-2-methyl-4-methylene-cyclohexane (13). Anhydrous potassium carbonate (134 mg, 970 μmol) was added to the stirred solution of protected mixture of enynes 12a and 12b (61.5 mg, 134.3 μmol; ratio of 1:2) in anhydrous THF/MeOH (1:1, 6 mL) at room temperature under argon. The stirring was continued for 19 h, then water and saturated NH$_4$Cl were added, the mixture was extracted with hexane, dried over MgSO$_4$ and concentrated. The residue was applied on a silica Sep-Pak cartridge and eluted with hexane. Further purification by HPLC (9.4 mm×25 cm Zorbax-Sil column, 4 mL/min) using hexane gave the enyne 13 (10.5 mg, 60% from 12a) collected at R$_V$ 22 mL.

13: $^1$H NMR (400 MHz, CDCl$_3$) δ 1.03 (9H, s, Si-t-Bu), 1.83 (3H, s, CH$_3$), 2.17 (2H, m), 2.38 (1H, m), 2.60 (1H, m), 3.09 (1H, s, ECH), 4.14 (1H, s, 3β-H), 4.38 and 4.67 (1H and 1H, each s, =CH$_2$), 7.37 (6H, m, Ar—H), 7.66 (4H, m, Ar—H); $^{13}$C NMR (100 MHz, CDCl$_3$) δ 19.49, 19.77, 27.03, 32.45, 73.59, 80.57, 83.65 110.95, 116.94, 127.30, 127.46, 129.57, 133.55, 134.07, 136.07, 136.26, 143.67, 146.46; HRMS (ESI) exact mass calcd for $C_{26}H_{30}OSiNa$ (M$^+$+Na) 409.1946, measured 409.1953

(m) Coupling of dienyne 13 with the triflate 14 (SCHEME II). 3-Desoxy-1α-[(tert-butyldiphenylsilyl)oxy]-2-methylene-25-[(triethylsilyl)oxy]-9,10-secocholesta-5(10),8-dien-6-yne (15). To a solution of acetylene 13 (10 mg, 26 μmol) and triflate 14 (10.6 mg, 20 μmol) in anhydrous DMF (200 μL) were added CuI (574 μg, 3.0 μmol), (PPh$_3$)$_2$Pd(OAc)$_2$ (430 μg, 0.57 μmol) and Et$_2$NH (200 μL) at room temperature under argon. After 30 min the mixture turned deep reddish-brown. Water was added and the mixture was extracted with hexane, dried over MgSO$_4$ and concentrated. The resulting product was applied on a silica Sep-Pak cartridge and eluted with hexane to afford trienyne 15 (11.5 mg, 74%).

$^1$H NMR (500 MHz, CDCl$_3$; vitamin D numbering) δ 0.56 (6H, q, J=7.7 Hz, 3×SiCH$_2$), 0.70 (3H, s, 18-H$_3$), 0.94 (9H, t, J=7.7 Hz, 3×SiCH$_2$CH$_3$), 1.02 (9H, s, Si-t-Bu), 1.19 (6H, s, 26- and 27-H$_3$), 1.81 (3H, s, 19-H$_3$), 4.15 (1H, s, 1β-H), 4.36 and 4.65 (1H and 1H, each s, =CH$_2$), 5.95 (1H, narr m, 9-H), 7.38 (6H, m, Ar—H), 7.67 (4H, m, Ar—H); HRMS (ESI) exact mass calcd for $C_{50}H_{74}O_2Si_2Na$ (M$^+$+Na) 786.5125, measured 786.5107.

(n) Hydrogenation of the trienyne 15 and thermal reaction of previtamin D compound 16. 3-Desoxy-1α-[(tert-butyldiphenylsilyl)oxy]-2-methylene-25-[(triethylsilyl)oxy]-vitamin D$_3$ (17). To a solution of the trienyne 15 (11 mg, 14.7 μmol) in hexane (1.4 mL) and quinoline (2.5 μL) was added Lindlar catalyst (34 mg). Mixture was stirred at room temperature under a positive pressure of hydrogen for 30 minutes, then it was applied on a silica Sep-Pak cartridge and eluted with hexane/ether (99.7:0.3) to yield previtamin D product 16 (9 mg, 80%). Silylated previtamin was then dissolved in anhydrous hexane (4.5 mL) and stirred at 65° C. for 5 h and at 40° C. overnight under argon. Solvent was evaporated and residue was purified by HPLC (9.4 mm×25 cm Zorbax-Sil column, 4 mL/min) using hexane/ethyl acetate (99:1) solvent system. Pure protected vitamin 17 (8.7 mg, 96%) was eluted at R$_V$ 16.3 mL.

$^1$H NMR (500 MHz, CDCl$_3$) δ 0.506 (3H, s, 18-H$_3$), 0.568 (6H, q, J=7.7 Hz, 3×SiCH$_2$), 0.951 (9H, t, J=7.7 Hz, 3×SiCH$_2$CH$_3$), 1.101 (9H, s, Si-t-Bu), 1.194 (6H, s, 26- and 27-H$_3$), 2.82 (1H, br d, J=12 Hz, 9β-H), 4.54 (1H, s, 1β-H), 5.13, 4.81 and 4.68 (1H, 2H and 1H, each s, 2×=CH$_2$), 6.30 and 5.99 (1H and 1H, each d, J=11.1 Hz, 7- and 6-H), 7.38 (6H, m, Ar—H), 7.67 (4H, m, Ar—H); HRMS (ESI) exact mass calcd for C$_{50}$H$_{76}$O$_2$Si$_2$Na (M$^+$+Na) 787.5281, measured 787.5276.

(o) Deprotection of hydroxyls in the vitamin D compound 17. 3-Desoxy-1α,25-dihydroxy-2-methylene-vitamin D$_3$ (18). To a solution of protected vitamin 17 (8.7 mg) in THF (0.7 mL) was added tetrabutylammonium fluoride (1.0 M in THF; 546 μL, 546 μmol) at room temperature under argon. The stirring was continued for 18 h, brine was added and the mixture was extracted with ethyl acetate. The organic extracts were dried over MgSO$_4$ and evaporated. The residue was purified by HPLC (9.4 mm×25 cm Zorbax-Sil column, 4 mL/min) using hexane/2-propanol (97:3) solvent system; vitamin 18 (1.554 mg, 33%) was collected at R$_V$ 25 mL. Analytical sample of the vitamin was obtained after HPLC (9.4 mm×25 cm Zorbax Eclipse XDB-C18 column, 4 mL/min) using methanol/water (93:7) solvent system (R$_V$ 42 mL).

18: UV (EtOH) λ$_{max}$ 268.5 nm; $^1$H NMR (400 MHz, CDCl$_3$) δ 0.550 (3H, s, 18-H$_3$), 0.938 (3H, d, J=6.5 Hz, 21-H$_3$), 1.218 (6H, s, 26- and 27-H$_3$), 2.23 (1H, m), 2, 33 (2H, m), 2.55 (1H, m), 2.83 (1H, br d, J~13 Hz, 9β-H), 4.56 (1H, d, J=4.6 Hz, 1β-H), 4.84, 4.96, 5.02 and 5.37 (each 1H, each s, 2×=CH$_2$), 6.06 and 6.37 (1H and 1H, each d, J=11.1 Hz, 7- and 6-H); HRMS (ESI) exact mass calcd for C$_{28}$H$_{44}$O$_2$Na (M$^+$+Na) 435.3239, measured 435.3243.

Example II

Preparation of (20S)-3-desoxy-1α,25-dihydroxy-2-methylene-vitamin D$_3$ (24)

(a) Conversion of the Grundmann ketone 19 to the enol triflate 20 (SCHEME III). (20S)-25-[(Triethylsilyl)oxy]-8-trifluoromethanesulfonyloxy-des-A,B-cholest-8-ene (20). A solution of the ketone 19 (28.5 mg, 72.19 μmol) in anhydrous THF (350 μL) was slowly added to the solution of LDA (2.0 M in THF/heptane/ethylbenzene; 40 μL, 80 μmol) in dry THF (100 μL) at −78° C. under argon. Then a solution of N-phenyltriflimide (28.3 mg, 79.27 μmol) in dry THF (100 μL) was added. After 2 h cooling bath was removed and reaction mixture was allowed to warm up to room temperature. Stirring was continued for 30 min and water was added. The mixture was extracted with hexane, dried over MgSO$_4$ and concentrated. The residue was applied on a silica Sep-Pak cartridge and eluted with hexane to afford the enol triflate 20 (17.2 mg, 82% considering recovered substrate) and unreacted ketone 19 (12 mg).

20: [α]$^{20}_D$-5.3° (c 0.86 CHCl$_3$); $^1$HNMR (200 MHz, CDCl$_3$) δ 0.564 (6H, q, J=8 Hz, 3×SiCH$_2$), 0.762 (3H, s, 18-H$_3$), 0.855 (3H, d, J=6.4 Hz, 21-H$_3$), 0.944 (9H, t, J=7.6 Hz, 3×SiCH$_2$CH$_3$), 1.18 (6H, s, 26- and 27-H$_3$), 1.789 (1H, m), 1.97 (2H, m), 2.30 (2H, m), 2.48 (1H, m), 5.66 (1H, dd, J=6.8, 3.4 Hz, 9-H); $^{13}$C NMR (50 MHz, CDCl$_3$) δ 6.98, 7.30, 11.68, 18.74, 20.83, 21.54, 24.07, 28.43, 30.02, 30.11, 35.01, 35.68, 35.94, 45.62, 50.36, 54.03, 73.54, 116.18, 150.16; HRMS (ESI) exact mass calcd for C$_{25}$H$_{45}$F$_3$O$_4$SSiNa (M$^+$+Na) 549.2658, measured 549.2637.

(h) Coupling of dienyne 13 with the triflate 20. (20S)-3-Desoxy-1α-[(tert-butyldiphenylsilyl)oxy]-2-methylene-25-[(triethylsilyl)oxy]-9,10-secocholesta-5(10),8-dien-6-yne (21). To a solution of dienyne 13 (19 mg, 49.1 μmol) and triflate 20 (12 mg, 22.77 μmol) in anhydrous DMF (390 μL) were added CuI (1.039 μg, 5.45 μmol), (PPh$_3$)$_2$Pd(OAc)$_2$ (817 μg, 1.09 μmol) and Et$_2$NH (382 μL) at room temperature under argon. After 30 min the mixture turned deep reddish-brown. Water was added and the mixture was extracted with hexane, dried over MgSO$_4$ and concentrated. The resulting product was applied on a silica Sep-Pak cartridge and eluted with hexane to afford trienyne 21 (10 mg, 58%).

15: $^1$H NMR (500 MHz, CDCl$_3$; vitamin D numbering) δ 0.559 (6H, q, J=7.7 Hz, 3×SiCH$_2$), 0.698 (3H, s, 18-H$_3$), 0.943 (9H, t, J=7.8 Hz, 3×SiCH$_2$CH$_3$), 1.023 (9H, s, Si-t-Bu), 1.187 (6H, s, 26- and 27-H$_3$), 1.808 (3H, s, 19-H$_3$), 4.15 (1H, s, 1β-H), 4.36 and 4.65 (1H and 1H, each s, =CH$_2$), 5.95 (1H, narr m, 9-H), 7.39 (6H, Ar—H), 7.69 (4H, m, Ar—H); HRMS (ESI) exact mass calcd for C$_{50}$H$_{74}$O$_2$Si$_2$Na (M$^+$+Na) 785.5125, measured 785.5143.

(i) Hydrogenation of the trienyne 21 and thermal reaction of previtamin D compound 22. (20S)-3-Desoxy-1α-[(tert-butyldiphenylsilyl)oxy]-2-methylene-25-[(triethylsilyl)oxy]-vitamin D$_3$ (23). To a solution of the trienyne 21 (10 mg, 13 μmol) in hexane (1.3 mL) and quinoline (2.2 μL) was added Lindlar catalyst (31 mg) and the mixture was stirred at room temperature under a positive pressure of hydrogen. After 30 min the mixture was applied on a silica Sep-Pak cartridge and eluted with hexane/ether (99:1) to give the silylated previtamin 23 (9 mg, 80%). The previtamin was then dissolved in anhydrous hexane (4.5 mL) and stirred at 65° C. for 5 h and at 40° C. overnight under argon. Solvent was evaporated and residue was applied on a silica Sep-Pak cartridge and eluted with hexane to give protected vitamin 23 (6.4 mg, 64%).

23: $^1$H NMR (500 MHz, CDCl$_3$) δ 0.503 (3H, s, 18-H$_3$), 0.563 (6H, q, J=7.7 Hz, 3×SiCH$_2$), 0.856 (3H, d, J=6.5 Hz, 21-H$_3$), 0.930 (9H, t, J=7.7 Hz, 3×SiCH$_2$CH$_3$), 1.025 (9H, s, Si-t-Bu), 1.188 (6H, s, 26- and 27-H$_3$), 2.82 (1H, br d, J=12 Hz, 9β-H), 4.54 (1H, s, 1β-H), 5.13, 4.81 and 4.68 (1H, 2H and 1H, each s, 2×=CH$_2$), 6.30 and 5.99 (1H and 1H, each d, J=11.1 Hz, 7- and 6-H), 7.38 (6H, m, Ar—H), 7.67 (4H, m, Ar—H); HRMS (ESI) exact mass calcd for C$_{50}$H$_{76}$O$_2$Si$_2$Na (M$^+$+Na) 787.5281, measured 787.5279.

(j) Deprotection of hydroxyls in the vitamin D compound 23. (20S)-3-Desoxy-1α,25-dihydroxy-2-methylene-vitamin D$_3$ (24). To a solution of protected vitamin 23 (6.4 mg, 8.36 μmol) in THF (0.5 mL) was added tetrabutylammonium fluoride (1.0 M in THF; 400 μL, 400 μmol) at room temperature under argon. The stirring was continued for 18 h, brine was added and the mixture was extracted with ethyl acetate. The organic extracts were dried over MgSO$_4$ and evaporated. The residue was purified by HPLC (9.4 mm×25 cm Zorbax-Sil column, 4 mL/min) using hexane/2-propanol (97:3) solvent system; vitamin 24 (1.95 mg, 56%) was collected at R$_V$ 36 mL. Analytical sample of the vitamin was obtained after reversed-phase HPLC (9.4 mm×25 cm Zorbax Eclipse XDB-C18 column, 4 mL/min) using methanol/water (91:9) solvent system (R$_V$ 56 mL).

24: UV (EtOH) λ$_{max}$ 266.8 nm; $^1$H NMR (500 MHz, CDCl$_3$) δ 0.549 (3H, s, 18-H$_3$), 0.851 (3H, d, J=6.5 Hz, 21-H$_3$), 1.215 (6H, s, 26- and 27-H$_3$), 1.75 (1H, d, J=6.0 Hz, OH), 1.85 (1H, m), 1.98 (2H, m), 2.23 (1H, ddd, J=18.9, 14.0, 7.5 Hz, 4β-H), 2.33 (2H, m), 2.57 (1H, dt, J=5.5, 12.4 Hz), 2.83 (1H, br d, J=12.5 Hz, 9β-H), 4.55 (1H, d, J=6.0 Hz, 1β-H), 4.84, 4.96, and 5.37 (2H, 1H and 1H, each narr t, J=1.5 Hz, 2×=CH$_2$), 5.02 (1H, s, =CH$_2$), 6.06 and 6.36 (1H and 1H, each d, J=11.0 Hz, 7- and 6-H); HRMS (ESI) exact mass calcd for C$_{28}$H$_{44}$O$_2$Na (M$^+$+Na) 435.3239, measured 435.3243.

SCHEME I, SCHEME II and SCHEME III are set forth below.

SCHEME I
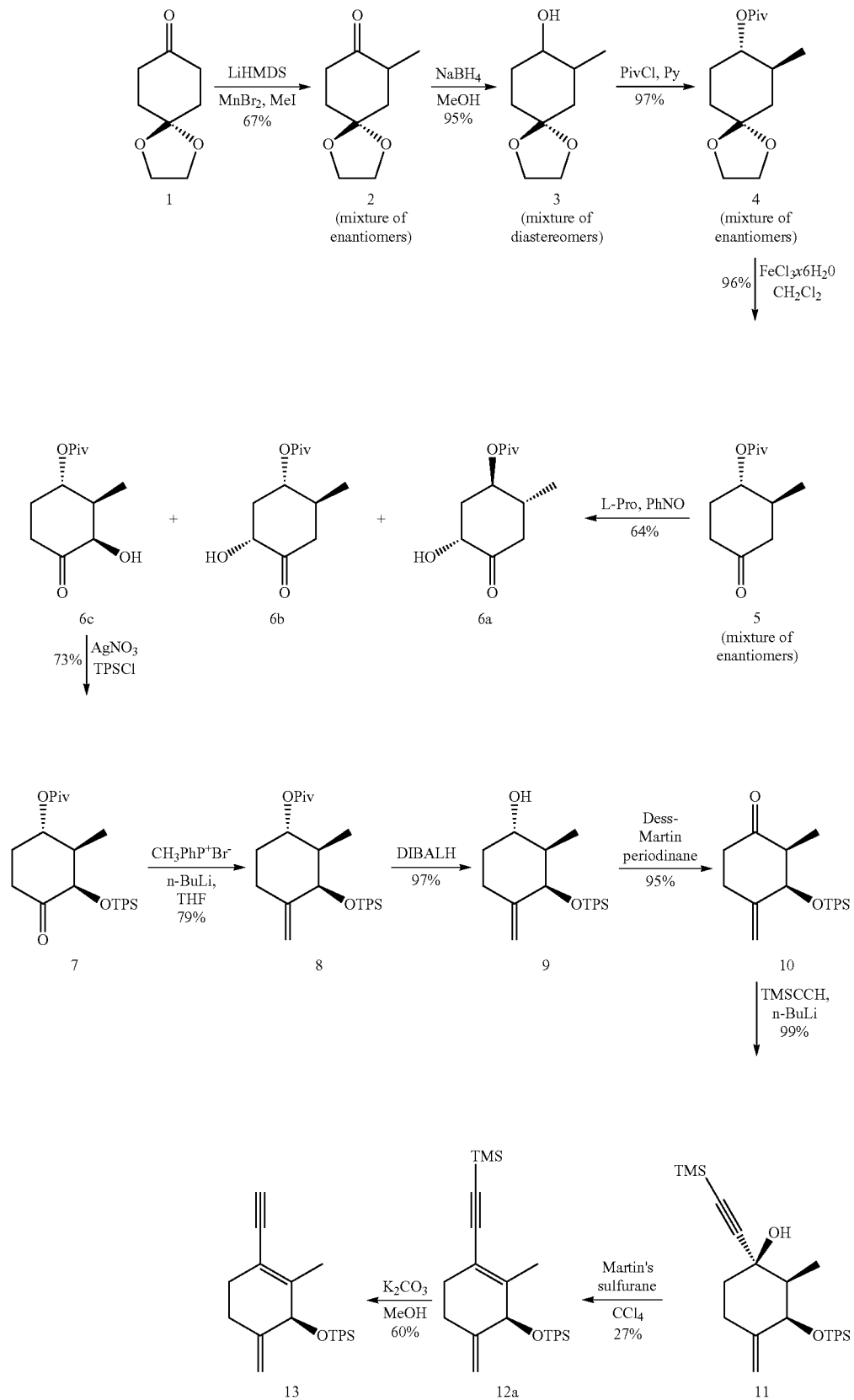

SCHEME II
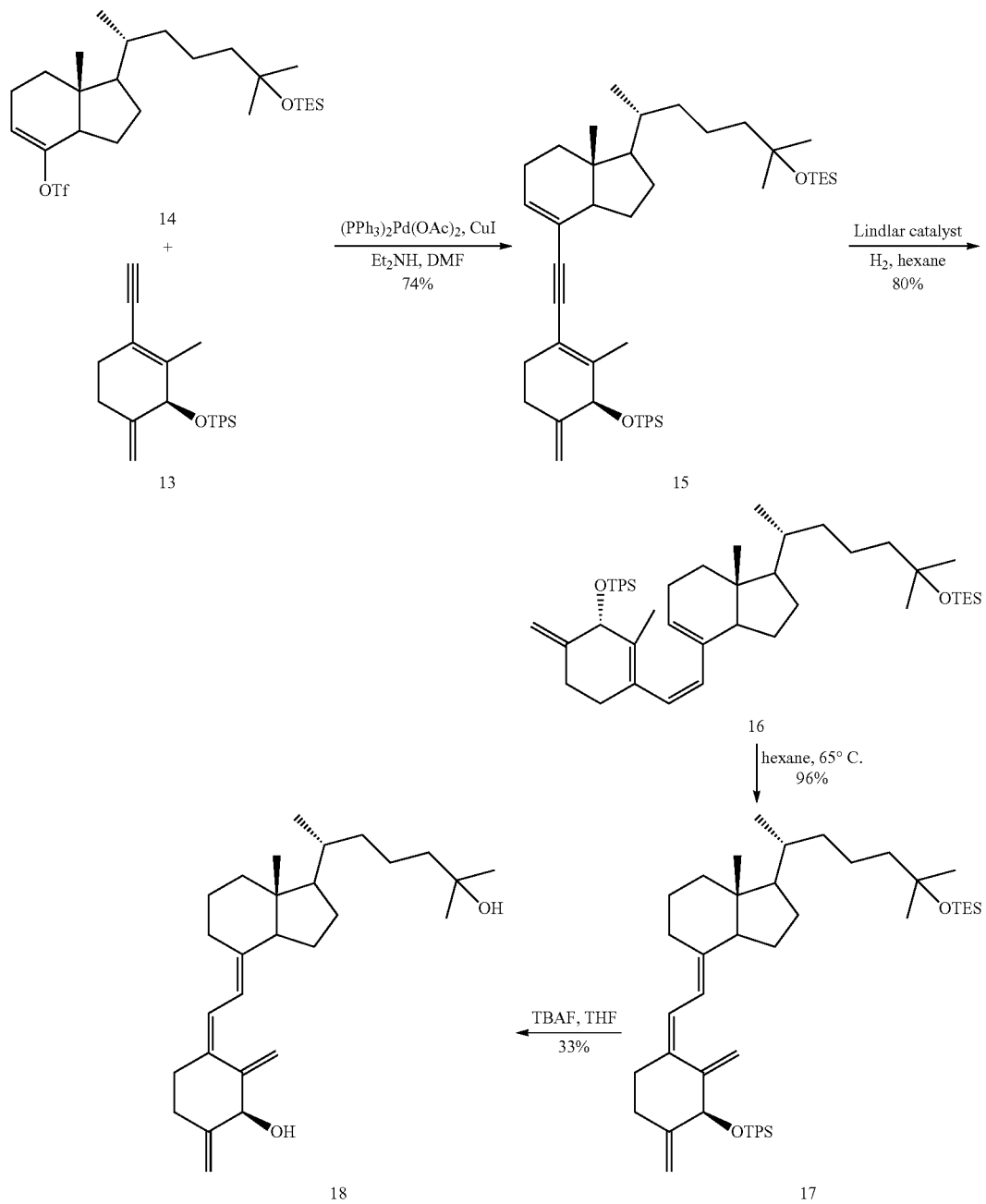
SCHEME III
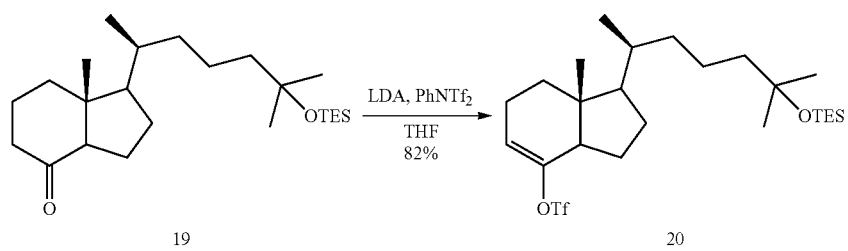

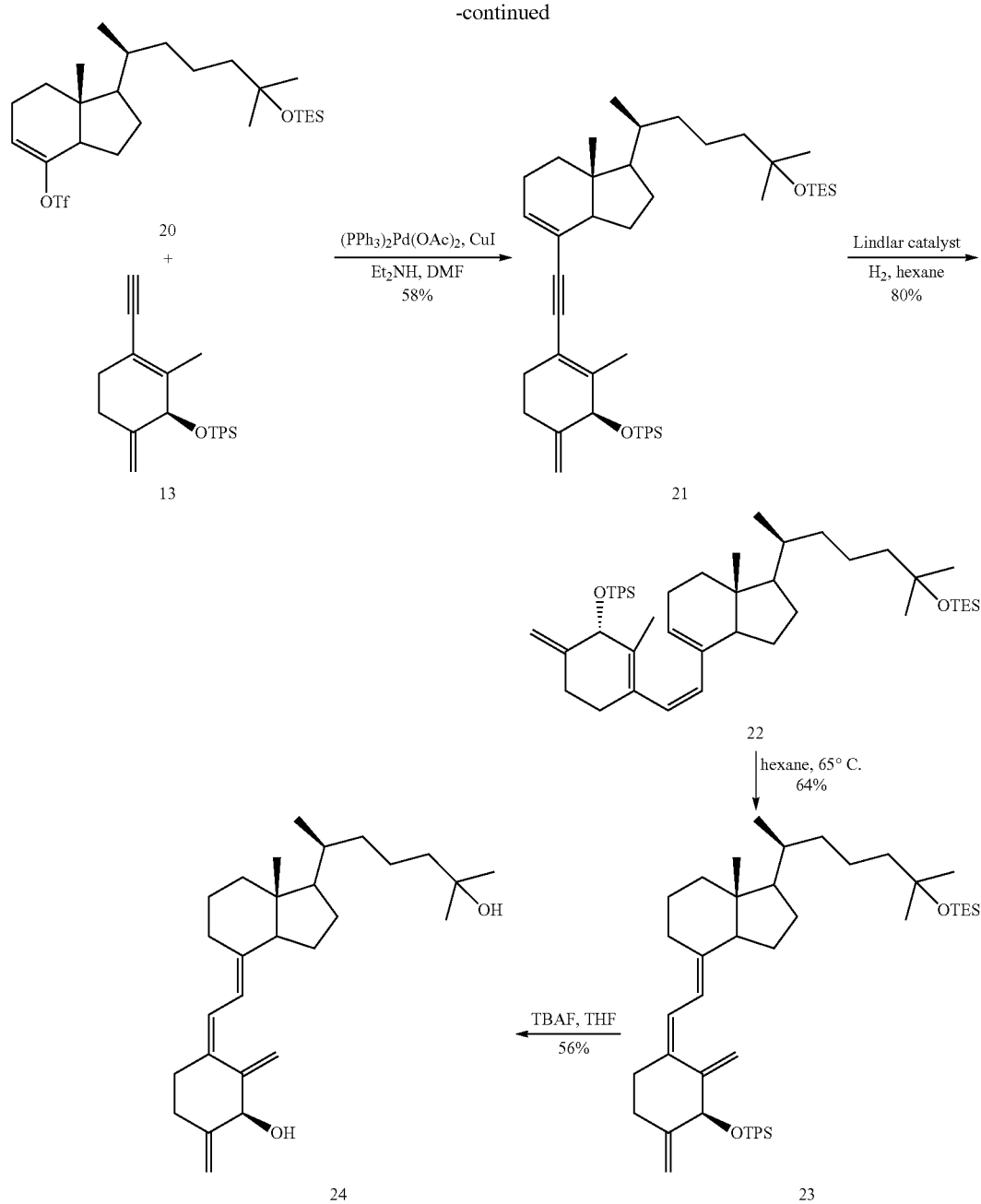

BIOLOGICAL ACTIVITY OF (20S)-3-DESOXY-1α,25-DIHYDROXY-2-METHYLENE-VITAMIN D₃ (3D-QMS)

The introduction of a methylene group to the 2-position, the removal of the hydroxyl group at carbon 3, and orienting the methyl group at carbon 20 in its epi or S configuration had little or no effect on binding to the full length recombinant rat vitamin D receptor, as compared to 1α,25-dihydroxyvitamin D₃. The compound 3D-QMS bound with about the same affinity to the receptor as compared to the standard 1,25-(OH)₂ D₃ (FIG. 1). It might be expected from these results that compound 3D-QMS would have equivalent biological activity. Surprisingly, however, compound 3D-QMS is a highly selective analog with unique biological activity.

Figure 5:
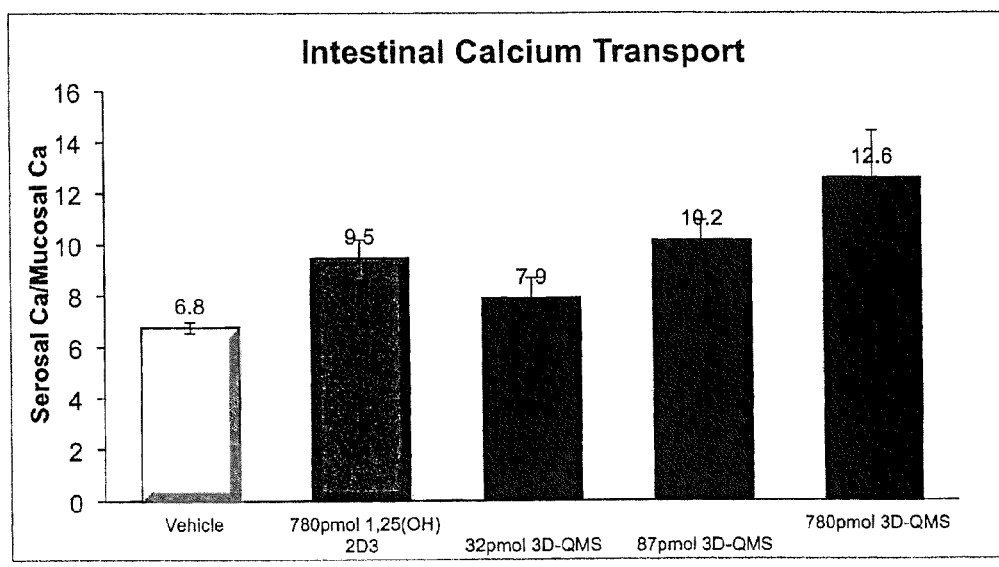

FIG. 5 shows that 3D-QMS has relatively high activity as compared to that of 1,25-dihydroxyvitamin D₃ (1,25(OH)₂ D₃), the natural hormone, in stimulating intestinal calcium transport. 3D-QMS is more potent than 1,25(OH)₂D₃ in promoting active calcium transport across the gut.

Figure 4:
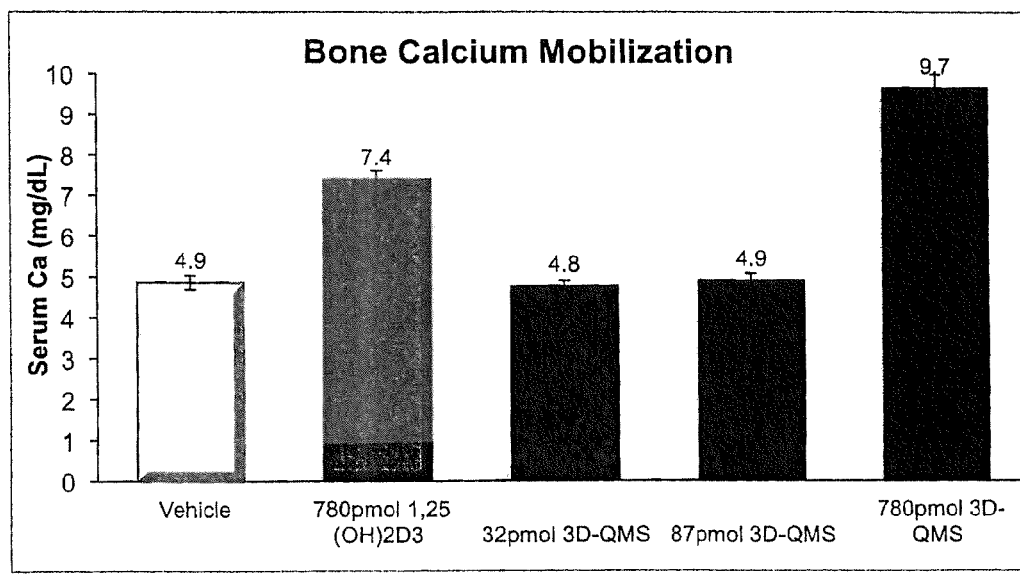

FIG. 4 demonstrates that 3D-QMS has relatively high bone calcium mobilization activity, as compared to 1,25(OH)₂D₃. 3D-QMS is more potent than the native hormone in releasing bone calcium stores.

Figure 2:
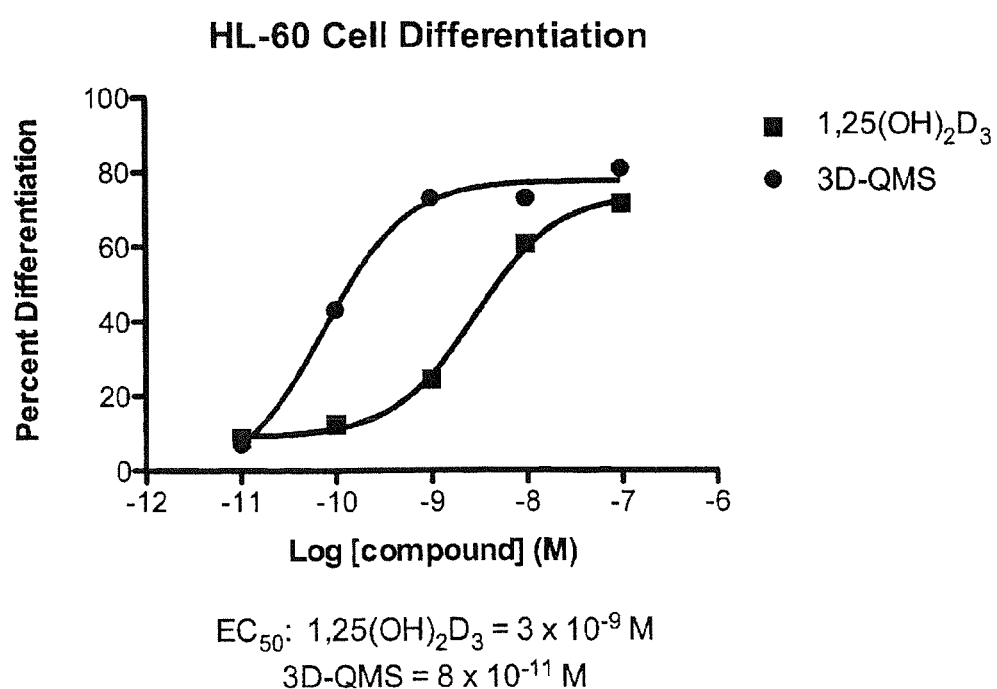

FIG. 2 illustrates that 3D-QMS is about 40 times more potent than 1,25(OH)₂D₃ on HL-60 cell differentiation, making it an excellent candidate for the treatment of a cancer, especially for the prevention or treatment of osteosarcoma, leukemia, colon cancer, breast cancer, skin cancer and prostate cancer.

Figure 3:
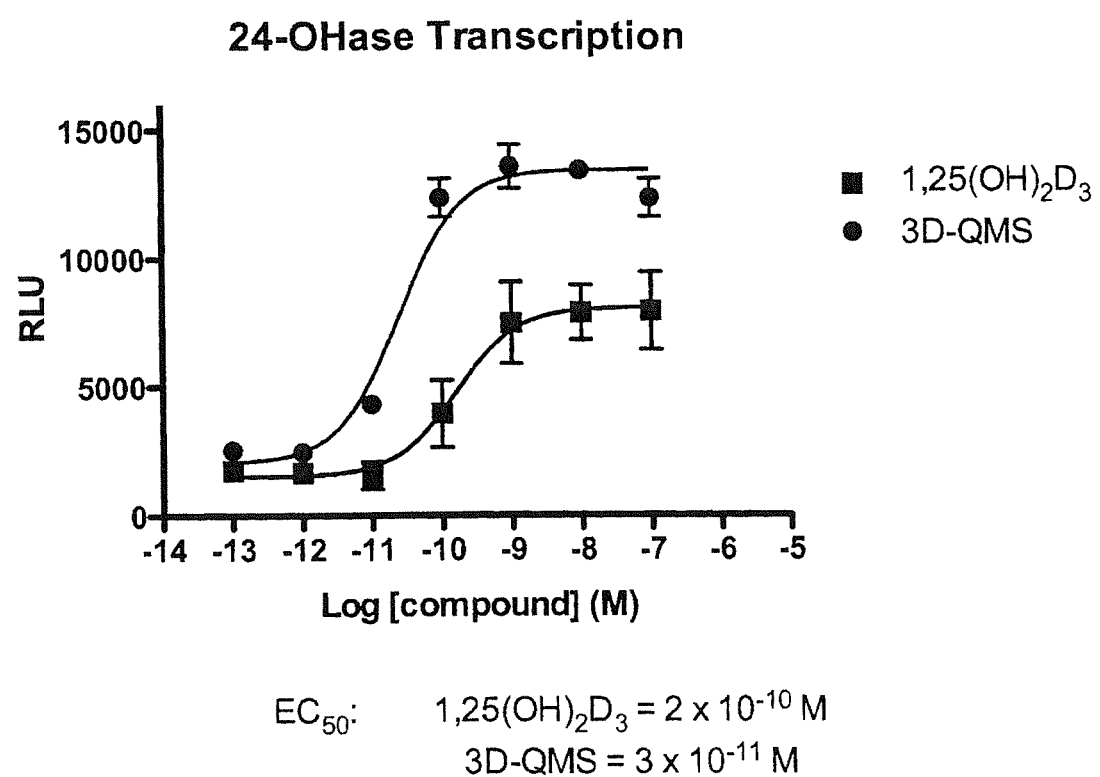

FIG. 3 illustrates that the compound 3D-QMS has about the same transcriptional activity as 1α,25-dihydroxyvitamin $D_3$ in bone cells. In bone cells, 3D-QMS is as potent as 1,25(OH)$_2$D$_3$ in increasing transcription of the 24-hydroxylase gene. This result, together with the cell differentiation activity of FIG. 2, suggests that 3D-QMS will be very effective in treating the above referred to cancers because it has direct cellular activity in causing cell differentiation, gene transcription, and in suppressing cell growth.

Experimental Methods

The compounds of the invention were prepared and studied using the following methods.

Vitamin D Receptor Binding

Test Material
Protein Source
Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCI) with 0.1% Chaps detergent. The receptor protein and ligand concentration was optimized such that no more than 20% of the added radiolabeled ligand was bound to the receptor.

Study Drugs
Unlabeled ligands were dissolved in ethanol and the concentrations determined using UV spectrophotometry (1,25 (OH)$_2$D$_3$: molar extinction coefficient=18,200 and $\lambda_{max}$=265 nm). Radiolabeled ligand ($^3$H-1,25(OH)$_2$D$_3$, ~159 Ci/mmole) was added in ethanol at a final concentration of 1 nM.

Assay Conditions
Radiolabeled and unlabeled ligands were added to 100 mcl of the diluted protein at a final ethanol concentration of ≤10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs
The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.

Cells
Human promyelocytic leukemia (HL60) cells were grown in RPMI-1640 medium containing 10% fetal bovine serum. The cells were incubated at 37° C. in the presence of 5% $CO_2$.

Assay Conditions
HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (Suda et al, J. Nutr. 100:1049, 1970) (0.47% Ca)+vitamins AEK for one week followed by Diet 11 (0.02% Ca)+vitamins AEK for 3 weeks. The rats were then switched to the same diet containing 0.47% Ca for one week followed by two weeks on the same diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined by atomic absorption spectrometry as a measure of bone calcium mobilization. The first 10 cm of the intestine was also collected for intestinal calcium transport analysis using the everted gut sac method.

Interpretation of Data

VDR Binding, HL60 Cell Differentiation, and Transcription Activity.
3D-QMS ($K_i$=3×10$^{-10}$M) has about the same activity as the natural hormone 1α,25-dihydroxyvitamin $D_3$ ($K_i$=1×10$^{-10}$M) in its ability to compete with [$^3$H]-1,25(OH)$_2$D$_3$ for binding to the full-length recombinant rat vitamin D receptor (FIG. 1). 3D-QMS is also about 40 times more potent (EC$_{50}$=8×10$^{-11}$M) in its ability (efficacy or potency) to promote HL60 differentiation as compared to 1α,25-dihydroxyvitamin $D_3$ (EC$_{50}$=3×10$^{-9}$M) (See FIG. 2). Also, compound 3D-QMS (EC$_{50}$=3×10$^{-11}$M) has about the same transcriptional activity in bone cells as 1α,25-dihydroxyvitamin $D_3$ (EC$_{50}$=2×10$^{-10}$M) (See FIG. 3). These data also indicate that 3D-QMS will have significant activity as an anti-cancer agent, especially for preventing or treating osteosarcoma, leukemia, colon cancer, breast cancer, skin cancer and prostate cancer because it has direct cellular activity in causing cell differentiation and in suppressing cell growth.

Calcium Mobilization from Bone and Intestinal Calcium Absorption in Vitamin D-Deficient Animals.
Using vitamin D-deficient rats on a low calcium diet (0.02%), the activities of 3D-QMS and 1,25(OH)$_2$D$_3$ in intestine and bone were tested. As expected, the native hormone (1,25(OH)$_2$D$_3$) increased serum calcium levels at the dosages tested (FIG. 4). FIG. 4 also shows that 3D-QMS has significantly more activity in mobilizing calcium from bone than 1,25(OH)$_2$D$_3$. Administration of 3D-QMS at 780 pmol/day for 4 consecutive days resulted in higher mobilization of bone calcium than the native hormone at the same 780 pmol/day dose in releasing bone calcium stores.

Intestinal calcium transport was evaluated in the same groups of animals using the everted gut sac method (FIG. 5). These results show that the compound 3D-QMS is more potent in promoting intestinal calcium transport activity when administered at the recommended lower dosages, as compared to 1,25(OH)$_2$D$_3$. Thus, it may be concluded that 3D-QMS has relatively high intestinal calcium transport activity at the tested doses.

These results further illustrate that 3D-QMS is an excellent candidate for numerous human therapies as described herein. 3D-QMS is an excellent candidate for treating a cancer because: (1) it has significant VDR binding, transcription activity and cellular differentiation activity; and (2) it is easily synthesized. Because of its selective activity in the bone and increased potency on cellular differentiation, 3D-QMS might also be useful in treatment of bone diseases, such as senile osteoporosis, postmenopausal osteoporosis, steroid-induced osteoporosis, low bone turnover osteoporosis, osteomalacia, and renal osteodystrophy.

BIOLOGICAL ACTIVITY OF (20R)-3-DESOXY-1α,25-DIHYDROXY-2-METHYLENE-VITAMIN D$_3$ (3D-QM)

Figure 6:
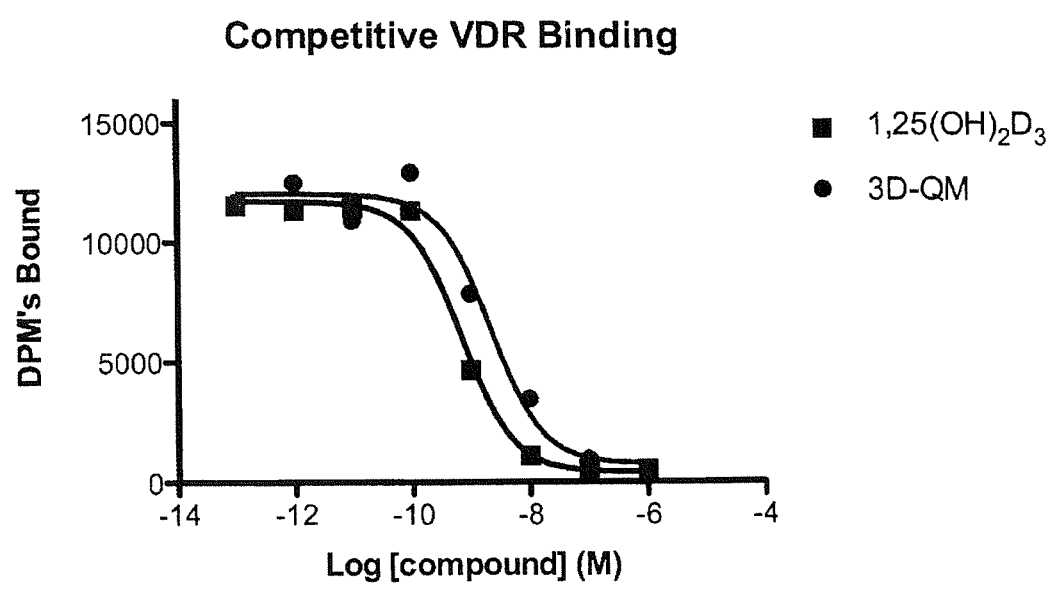
FIGS. 6-10 illustrate various biological activities of (20R)-3-desoxy-1α, 25-dihydroxy-2-methylene-vitamin $D_3$, hereinafter referred to as "3D-QM," as compared to the native hormone 1α,25-dihydroxyvitamin $D_3$, hereinafter "1,25 $(OH)_2D_3$."

The introduction of a methylene group to the 2-position, the removal of the hydroxyl group at carbon 3, and orienting the methyl group at carbon 20 in its natural or R configuration had little or no effect on binding to the full length recombinant rat vitamin D receptor, as compared to 1α,25-dihydroxyvitamin D$_3$. The compound 3D-QM bound with about the same affinity to the receptor as compared to the standard 1,25(OH)$_2$D$_3$ (FIG. 6). It might be expected from these results that compound 3D-QM would have equivalent biological activity. Surprisingly, however, compound 3D-QM is a highly selective analog with unique biological activity.

Figure 10:
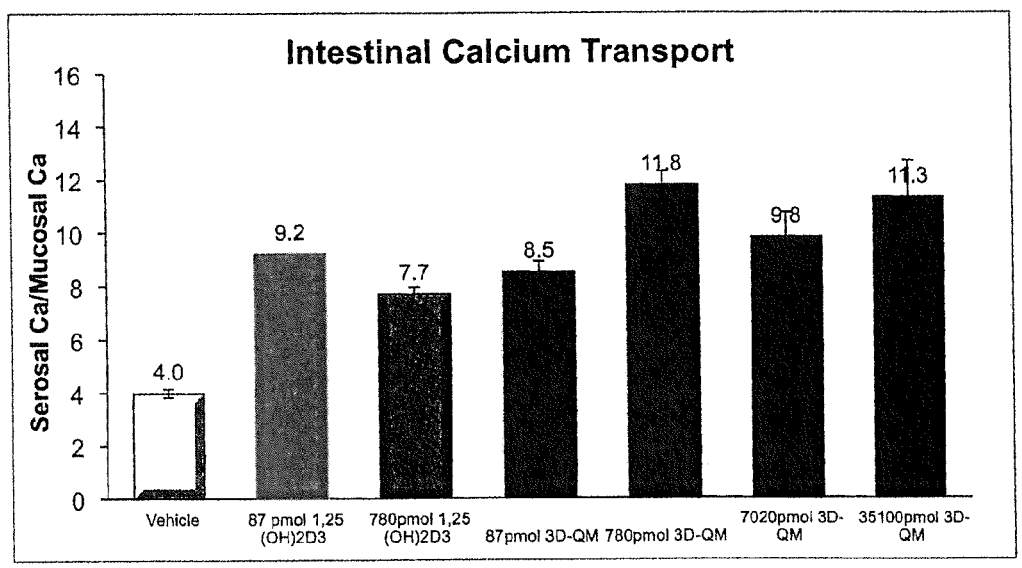

FIG. 10 shows that 3D-QM has relatively high activity in stimulating intestinal calcium transport. 3D-QM has only slightly less potency as 1,25(OH)$_2$D$_3$ in promoting active calcium transport across the gut.

Figure 9:
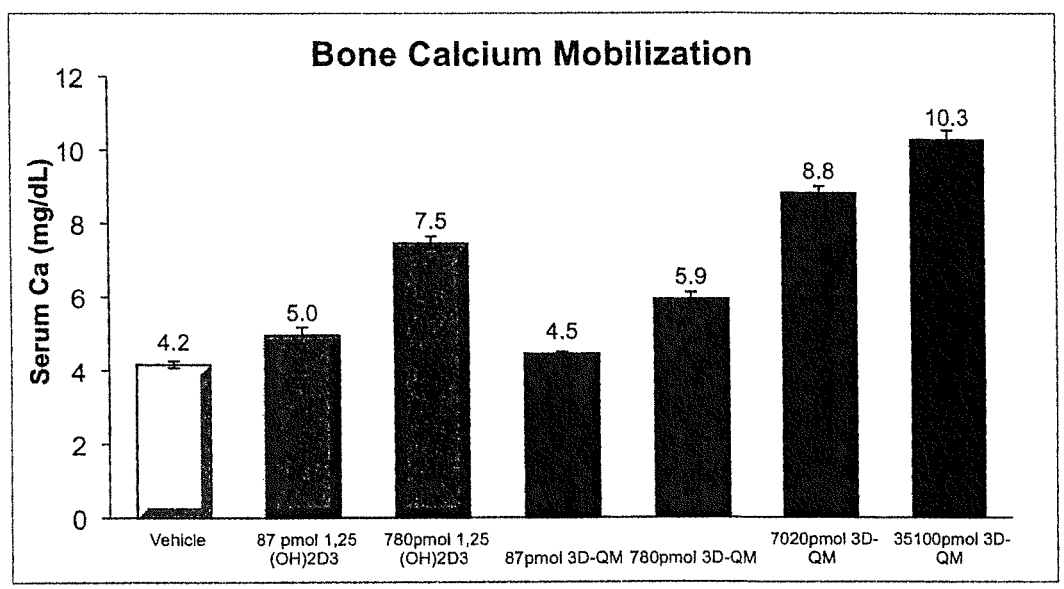

FIG. 9 demonstrates that 3D-QM has relatively high bone calcium mobilization activity, as compared to 1,25(OH)$_2$D$_3$. 3D-QM has about the same potency as the native hormone in releasing bone calcium stores.

Figure 7:
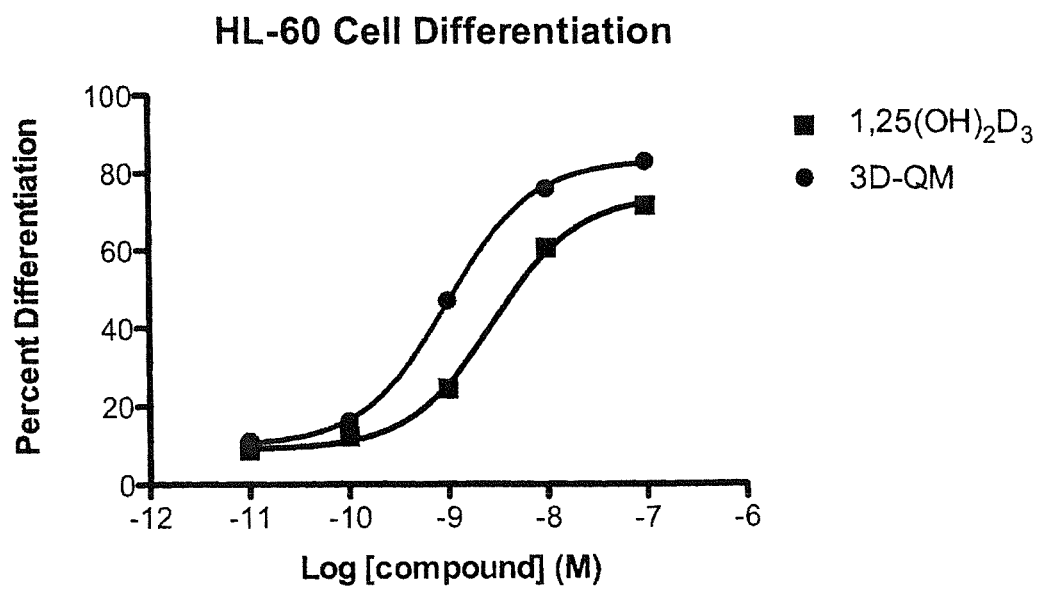

FIG. 7 illustrates that 3D-QM has about the same potency as 1,25(OH)$_2$D$_3$ on HL-60 cell differentiation, making it an excellent candidate for the treatment of a cancer, especially for the prevention or treatment of osteosarcoma, leukemia, colon cancer, breast cancer, skin cancer and prostate cancer.

Figure 8:
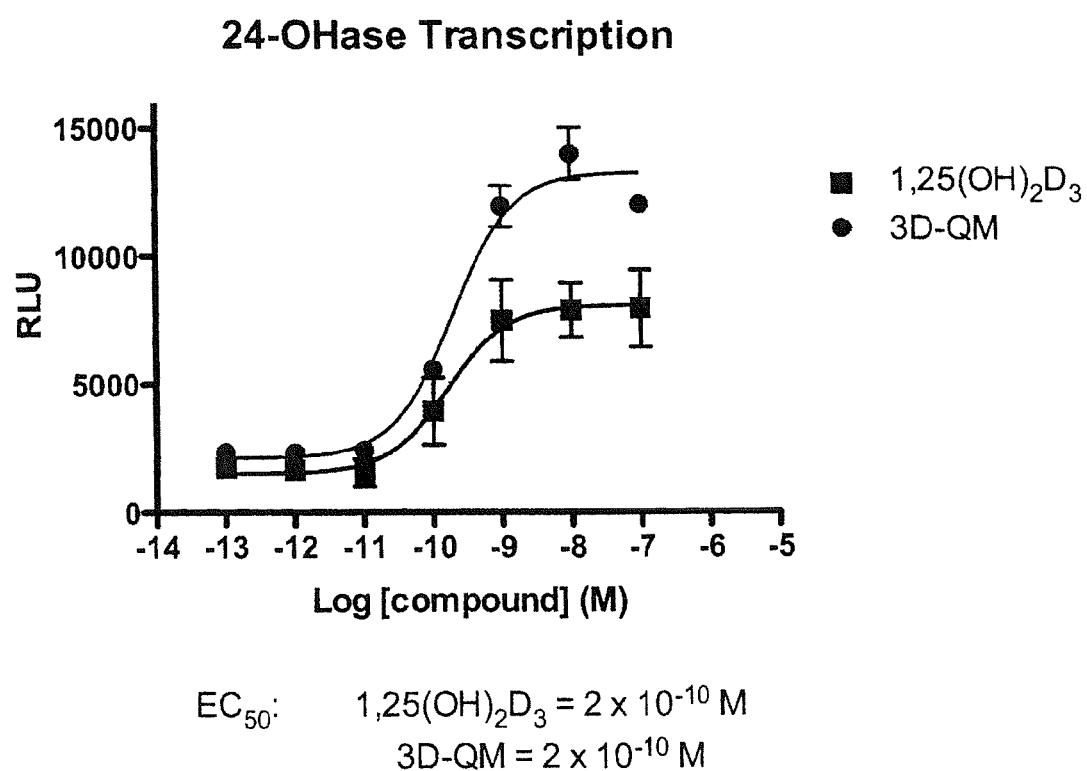

FIG. 8 illustrates that the compound 3D-QM has about the same transcriptional activity as 1α,25-dihydroxyvitamin D$_3$ in bone cells. In bone cells, 3D-QM is as potent as 1,25(OH)$_2$D$_3$ in increasing transcription of the 24-hydroxylase gene. This result, together with the cell differentiation activity of FIG. 7, suggests that 3D-QM will be very effective in treating the above referred to cancers because it has direct cellular activity in causing cell differentiation, gene transcription, and in suppressing cell growth.

Interpretation of Data

VDR Binding, HL60 Cell Differentiation, and Transcription Activity.

3D-QM 3D-QM ($K_i$=4×10$^{-10}$M) has about the same activity as the natural hormone 1α,25-dihydroxyvitamin D$_3$ ($K_i$=1×10$^{-10}$M) in its ability to compete with [$^3$H]-1,25(OH)$_2$D$_3$ for binding to the full-length recombinant rat vitamin D receptor (FIG. 6). 3D-QM is also about equivalent (EC$_{50}$=1×10$^{-9}$M) in its ability (efficacy or potency) to promote HL60 differentiation as compared to 1α,25-dihydroxyvitamin D$_3$ (EC$_{50}$=3×10$^{-9}$M) (See FIG. 7). Also, compound 3D-QM (E$_{50}$=2×10$^{-10}$M) has about the same transcriptional activity in bone cells as 1α,25-dihydroxyvitamin D$_3$ (EC$_{50}$=2×10$^{-1}$M) (See FIG. 8). These data also indicate that 3D-QM will have significant activity as an anti-cancer agent, especially for preventing or treating osteosarcoma, leukemia, colon cancer, breast cancer, skin cancer and prostate cancer because it has direct cellular activity in causing cell differentiation and in suppressing cell growth.

Calcium Mobilization from Bone and Intestinal Calcium Absorption in Vitamin D-Deficient Animals.

Using vitamin D-deficient rats on a low calcium diet (0.02%), the activities of 3D-QM and 1,25(OH)$_2$D$_3$ in intestine and bone were tested. As expected, the native hormone (1,25(OH)$_2$D$_3$) increased serum calcium levels at the dosages tested (FIG. 9). FIG. 9 also shows that 3D-QM has significant activity in mobilizing calcium from bone. Administration of 3D-QM at 87 pmol/day for 4 consecutive days resulted in only slightly less mobilization of bone calcium than the native hormone at the same 87 pmol/day dose in releasing bone calcium stores.

Intestinal calcium transport was evaluated in the same groups of animals using the everted gut sac method (FIG. 10). These results show that the compound 3D-QM is more potent in promoting intestinal calcium transport activity when administered at the recommended lower dosages, as compared to 1,25(OH)$_2$D$_3$. Thus, it may be concluded that 3D-QM has relatively high intestinal calcium transport activity at the tested doses.

These results further illustrate that 3D-QM is an excellent candidate for numerous human therapies as described herein. 3D-QM is an excellent candidate for treating a cancer because: (1) it has significant VDR binding, transcription activity and cellular differentiation activity; and (2) it is easily synthesized. Because of its selective activity in the intestine and bone and increased potency on cellular differentiation, 3D-QM might also be useful in treatment of bone diseases, such as senile osteoporosis, postmenopausal osteoporosis, steroid-induced osteoporosis, low bone turnover osteoporosis, osteomalacia, and renal osteodystrophy.

For prevention and/or treatment purposes, the compounds of this invention defined by formula I, Ia, and Ib may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 3D-QMS of formula Ia and 3D-QM of formula Ib, may be administered orally, topically, parenterally, rectally, nasally, sublingually, or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I, particularly 3D-QMS and 3D-QM, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly 3D-QMS and 3D-QM, as defined by the above formula I, Ia, and Ib, as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually or parenterally in dosages of from about 0.01 μg/day to about 1000 μg/day, and preferably from about 0.1 μg/day to about 500 μg/day.

The compounds I, particularly 3D-QMS and 3D-QM, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 3D-QMS and 3D-QM, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:
1. A compound having the formula:

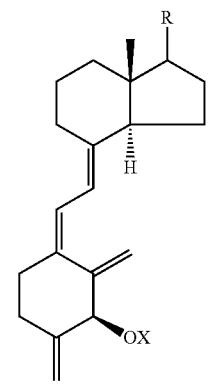

where X is selected from the group consisting of hydrogen and a hydroxy-protecting group, and where R may be hydrogen, an alkyl, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

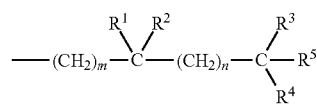

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH—)$_q$—, were q is an integer from 2 to 5, and where R$^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —CR$_1$R$_2$— or (CH$_2$)$_n$— at positions 20, 22, and 21, respectively, may be replaced by an oxygen or sulfur atom.

2. The compound of claim 1 wherein X is hydrogen.

3. The compound of claim 1 wherein R is selected from:

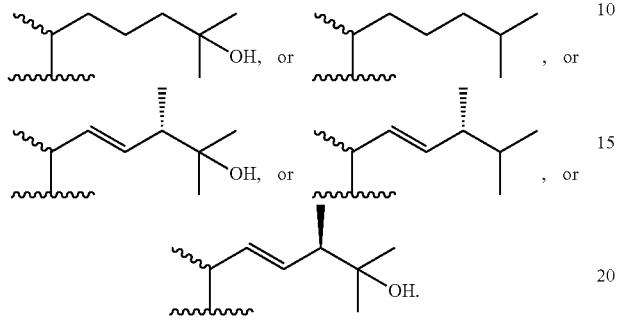

4. The compound of claim 3 wherein X is hydrogen.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 μg to about 1000 μg per gram of composition.

7. The pharmaceutical composition of claim 5 wherein said effective amount comprises from about 0.1 μg to about 500 μg per gram of composition.

8. A compound having the formula:

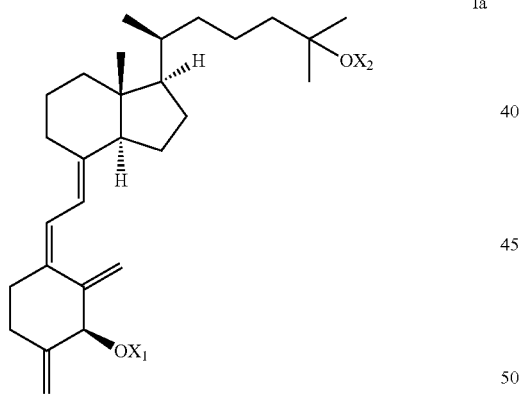

where X$_1$ and X$_2$, which may be the same or different, are each selected from hydrogen or a hydroxy-protecting group.

9. The compound of claim 8 wherein X$_2$ is hydrogen.

10. The compound of claim 8 wherein X$_1$ is hydrogen.

11. The compound of claim 8 wherein X$_1$ and X$_2$ are both t-butyldimethylsilyl.

12. A pharmaceutical composition containing an effective amount of at least one compound as claimed in claim 8 together with a pharmaceutically acceptable excipient.

13. The pharmaceutical composition of claim 12 wherein said effective amount comprises from about 0.01 μg to about 1000 μg per gram of composition.

14. The pharmaceutical composition of claim 12 wherein said effective amount comprise from about 0.1 μg to about 500 μg per gram of composition.

15. A compound having the formula:

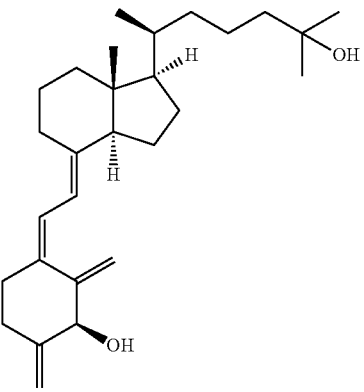 [SMILES: C=C1CC/C(=C/C=C2\CCC[C@]3(C)[C@@H]([C@@H](C)CCCC(C)(C)O)CC[C@@H]23)C(=C)[C@H]1O]

and named (20S)-3-desoxy-1α,25-dihydroxy-2-methylene-vitamin D$_3$.

16. A pharmaceutical composition containing an effective amount of (20S)-3-desoxy-1α,25-dihydroxy-2-methylene-vitamin together with a pharmaceutically acceptable excipient.

17. The pharmaceutical composition of claim 16 wherein said effective amount comprises from about 0.01 μg to about 1000 μg per gram of composition.

18. The pharmaceutical composition of claim 16 wherein said effective amount comprises from about 0.1 μg to about 500 μg per gram of composition.

19. A method of treating a disease selected from the group consisting of osteosarcoma, leukemia, colon cancer, breast cancer, skin cancer or prostate cancer comprising, administering to a subject with said disease an effective amount of a 3-desoxy-2-methylene-vitamin D analog having the formula:

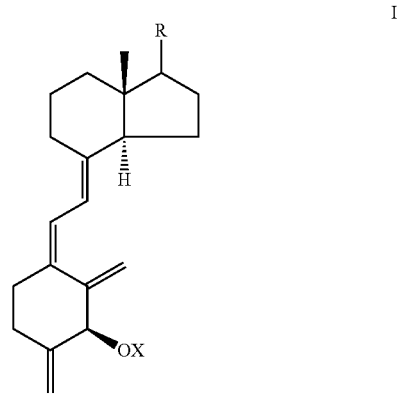

where X is selected from the group consisting of hydrogen and a hydroxy-protecting group, and where R may be hydrogen, an alkyl, hydroxyalkyl or fluoroalkyl group, or R may represent a side chain of the formula:

where the stereochemical center at carbon 20 may have the R or S configuration, and where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR⁵ and a radical of the structure:

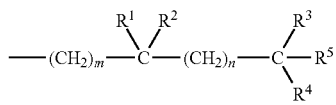

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deutemalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom or where any of the groups —CH(CH₃)—, —$(CH_2)_m$—, $CR_1R_{2-}$— or —$(CH_2)_n$— at positions 20, 22, and 23, respectively, may be replaced by an oxygen or sulfur atom.

20. The method of claim 19 wherein the vitamin D analog is administered orally.
21. The method of claim 19 wherein the vitamin D analog is administered parenterally.
22. The method of claim 19 wherein the vitamin D analog is administered transdermally.
23. The method of claim 19 wherein the vitamin D analog is administered rectally.
24. The method of claim 19 wherein the vitamin D analog is administered nasally.
25. The method of claim 19 wherein the vitamin analog is administered sublingually.
26. The method of claim 19 wherein the vitamin D analog is administered in a dosage of from about 0.01 µg/day to about 1000 µg/day.
27. The method of claim 19 wherein the vitamin D analog has the formula:

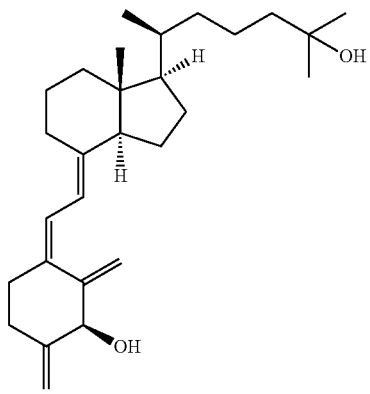 [SMILES: C=C1CC/C(=C/C=C2\CCC[C@]3(C)[C@@H]([C@@H](C)CCCC(C)(C)O)CC[C@@H]23)C(=C)[C@H]1O]

and is named (20S)-3-desoxy-1α,25-dihydroxy-2-methylene-vitamin D₃.

28. The method of claim 19 wherein the vitamin D analog has the formula:

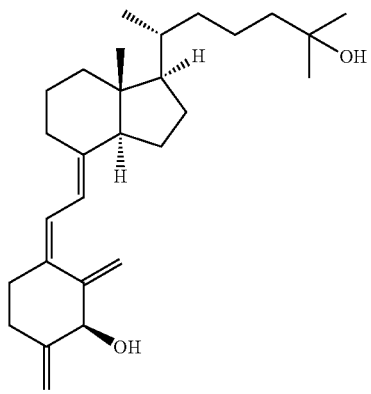 [SMILES: C=C1CC/C(=C/C=C2\CCC[C@]3(C)[C@@H]([C@H](C)CCCC(C)(C)O)CC[C@@H]23)C(=C)[C@H]1O]

and is named (20R)-3-desoxy-1α,25-dihydroxy-2-methylene-vitamin D₃.

29. A method of treating metabolic bone disease where it is desired to maintain or increase bone mass comprising administering to a patient with said disease an effective amount of a compound having the formula:

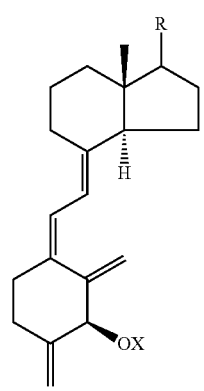

where X is selected from the group consisting of hydrogen and a hydroxy-protecting group, and where R may be hydrogen, an alkyl, hydroxyalkyl or fluoroalkyl group, or R may represent a side chain of the formula:

where the stereochemical center at carbon 20 may have the R or S configuration, and where Z is selected from Y, —OY, —CH₂OY, —C≡CY and —CH=CHY, where the double bond may have the cis or trans geometry, and where is selected from hydrogen, methyl, —COR⁵ and a radical of the structure:

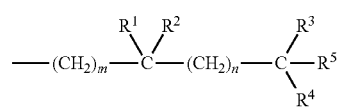

where m and n, independently, represent the integers from 0 to 5, where $R^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$-alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$, —(CH$_2$)$_n$— or (CR$_1$R$_2$)— at positions 20, 22, and 23, respectively, may be replaced by an oxygen or sulfur atom.

30. The method of claim 29 where the disease is senile osteoporosis.
31. The method of claim 29 where the disease is postmenopausal osteoporosis.
32. The method of claim 29 where the disease is steroid-induced osteoporosis.
33. The method of claim 29 were the disease is low bone turnover osteoporosis.
34. The method of claim 29 where the disease is osteomalacia.
35. The method of claim 29 where the disease is renal osteodystrophy.
36. The method of claim 29 wherein the compound is administered orally.
37. The method of claim 29 wherein the compound is administered parenterally.
38. The method of claim 29 wherein the compound is administered transdermally.
39. The method of claim 29 wherein the compound is administered rectally.
40. The method of claim 29 wherein the compound is administered nasally.
41. The method of claim 29 wherein the compound is administered sublingually.
42. The method of claim 29 wherein the compound is administered in a dosage of from about 0.01 µg/day to about 1000 µg/day.
43. The method of claim 29 wherein the compound has the formula

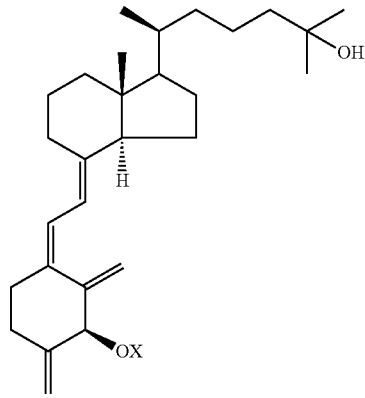

and is named (20S)-3-desoxy-1α,25-dihydroxy-2-methylene-Vitamin D$_3$.

44. The method of claim 29 wherein the compound has the formula

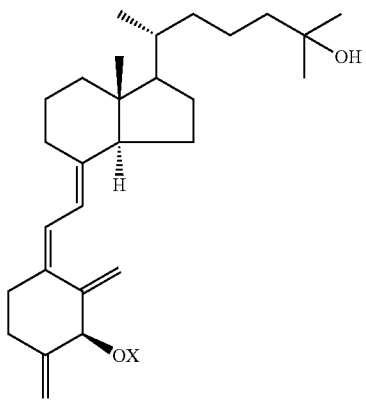

and is named (20R)-3-desoxy-1α,25-dihydroxy-2-methylene-vitamin D$_3$.

45. A compound having the formula:

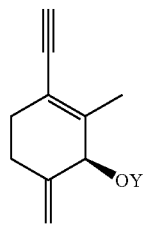

where Y is a hydroxy-protecting group.
46. The compound of claim 45 wherein Y is t-butyidiphenylsilyl.
47. A compound having the formula:

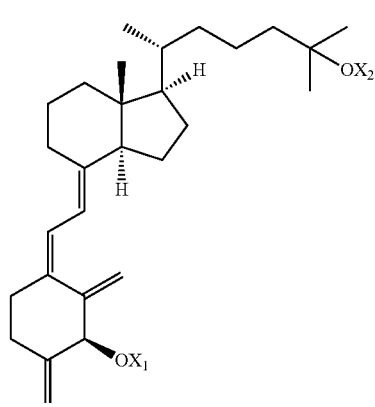

where X$_1$ and X$_2$ Which may be the same or different, are each selected from hydrogen or a hydroxy-protecting group.
48. The compound of claim 47 wherein X$_2$ is hydrogen.
49. The compound of claim 47 wherein X$_1$ is hydrogen.
50. The compound of claim 47 wherein X$_1$ and X$_2$ are both t-butyldimethylsilyl.
51. A pharmaceutical composition containing an effective amount of at least one compound as claimed in claim 47 together with a pharmaceutically acceptable excipient.
52. The pharmaceutical composition of claim 51 wherein said effective amount comprises from about 0.01 µg to about 1000 µg per grain of composition.
53. The pharmaceutical composition of claim 51 wherein said effective amount comprise from about 0.1 µg to about 500 µg per gram of composition.

54. A compound having the formula:

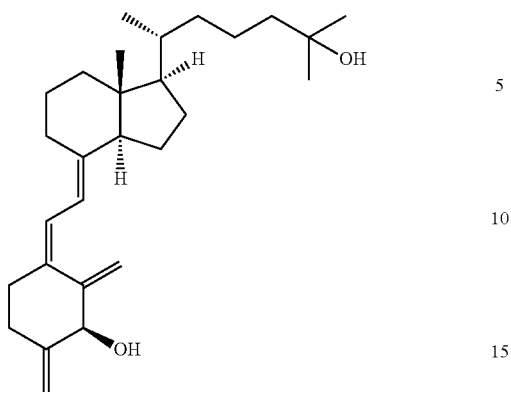

and named (20R)-3-desoxy-1α,25-dihydroxy-2-methylene-vitamin $D_3$.

55. A pharmaceutical composition containing, an effective amount of (20R)-3-desoxy-1α,25-dihydroxy-2-methylene-vitamin $D_3$ together with a pharmaceutically acceptable excipient.

56. The pharmaceutical composition of claim 55 wherein said effective amount comprises from about 0.01 μg to about 1000 μg per gram of composition.

57. The pharmaceutical composition of claim 55 wherein said effective amount comprises from about 0.1 μg to about 500 μg per gram of composition.

* * * * *